(12) United States Patent
Govindan et al.

(10) Patent No.: US 9,272,057 B2
(45) Date of Patent: *Mar. 1, 2016

(54) COMBINING RADIOIMMUNOTHERAPY AND ANTIBODY-DRUG CONJUGATES FOR IMPROVED CANCER THERAPY

(71) Applicant: Immunomedics, Inc., Morris Plains, NJ (US)

(72) Inventors: Serengulam V. Govindan, Summit, NJ (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/624,683

(22) Filed: Feb. 18, 2015

(65) Prior Publication Data

US 2015/0165075 A1 Jun. 18, 2015

Related U.S. Application Data

(60) Division of application No. 14/029,165, filed on Sep. 17, 2013, now Pat. No. 8,992,931, which is a division of application No. 13/855,213, filed on Apr. 2, 2013, now Pat. No. 8,586,050, which is a division of application No. 12/957,655, filed on Dec. 1, 2010, now Pat. No. 8,435,529, which is a continuation-in-part of application No. 12/537,803, filed on Aug. 7, 2009, now Pat. No. 8,491,896, which is a continuation-in-part of application No. 11/849,791, filed on Sep. 4, 2007, now abandoned, which is a division of application No. 10/461,885, filed on Jun. 16, 2003, now Pat. No. 7,282,567, said application No. 12/957,655 is a continuation-in-part of application No. 12/389,503, filed on Feb. 20, 2009, now Pat. No. 8,084,583, which is a continuation of application No. 11/745,896, filed on May 8, 2007, now Pat. No. 7,517,964, which is a division of application No. 10/377,121, filed on Mar. 3, 2003, now Pat. No. 7,238,785, said application No. 12/957,655 is a continuation-in-part of application No. 12/629,404, filed on Dec. 2, 2009, now Pat. No. 7,999,083, which is a continuation-in-part of application No. 12/026,811, filed on Feb. 6, 2008, now Pat. No. 7,591,994, which is a continuation-in-part of application No. 11/388,032, filed on Mar. 23, 2006, (Continued)

(51) Int. Cl.
| | |
|---|---|
| A61K 39/00 | (2006.01) |
| A61K 51/10 | (2006.01) |
| A61K 47/48 | (2006.01) |
| B82Y 5/00 | (2011.01) |
| C07K 16/30 | (2006.01) |
| C07K 16/44 | (2006.01) |
| A61K 31/7068 | (2006.01) |
| A61K 39/395 | (2006.01) |
| A61K 41/00 | (2006.01) |
| A61K 45/06 | (2006.01) |
| A61K 51/08 | (2006.01) |
| A61K 31/4745 | (2006.01) |

(52) U.S. Cl.
CPC ......... *A61K 51/1057* (2013.01); *A61K 31/4745* (2013.01); *A61K 31/7068* (2013.01); *A61K 39/39558* (2013.01); *A61K 41/0038* (2013.01); *A61K 45/06* (2013.01); *A61K 47/484* (2013.01); *A61K 47/486* (2013.01); *A61K 47/4843* (2013.01); *A61K 47/48284* (2013.01); *A61K 47/48384* (2013.01); *A61K 47/48415* (2013.01); *A61K 47/48423* (2013.01); *A61K 47/48438* (2013.01); *A61K 47/48484* (2013.01); *A61K 47/48592* (2013.01); *A61K 51/08* (2013.01); *A61K 51/109* (2013.01); *A61K 51/1096* (2013.01); *B82Y 5/00* (2013.01); *C07K 16/30* (2013.01); *C07K 16/303* (2013.01); *C07K 16/3092* (2013.01); *C07K 16/44* (2013.01); *A61K 2039/505* (2013.01); *A61K 2039/507* (2013.01); *A61K 2300/00* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 4,359,457 A | 11/1982 | Neville et al. | |
| 4,935,498 A | 6/1990 | Sessler et al. | |

(Continued)

FOREIGN PATENT DOCUMENTS

| | | |
|---|---|---|
| DE | 10034607 | 2/2002 |
| EP | 0253202 | 1/1988 |

(Continued)

OTHER PUBLICATIONS

Linnenbach et al. (PNAS, vol. 86, 1989, pp. 27-31).*

(Continued)

*Primary Examiner* — Laura B Goddard
*Assistant Examiner* — Meera Natarajan
(74) *Attorney, Agent, or Firm* — Richard A. Nakashima

(57) ABSTRACT

Described herein are compositions and methods of use of radionuclide-antibody conjugates (for RAIT) and drug-antibody conjugates (ADC). The combination of RAIT and ADC was more efficacious than either RAIT alone, ADC alone, or the sum of effects of RAIT and ADC. The unexpected synergy resulted in decreased tumor growth rate and increased survival, with a high incidence of tumor-free survival in Capan-1 human pancreatic cancer xenografts in nude mice.

12 Claims, 12 Drawing Sheets

Related U.S. Application Data now Pat. No. 8,877,901, and a continuation-in-part of application No. 10/734,589, filed on Dec. 15, 2003, now Pat. No. 7,585,491.

(60) Provisional application No. 60/388,314, filed on Jun. 14, 2002, provisional application No. 61/087,463, filed on Aug. 8, 2008, provisional application No. 61/144,227, filed on Jan. 13, 2009, provisional application No. 60/360,229, filed on Mar. 1, 2002, provisional application No. 60/668,603, filed on Apr. 6, 2005, provisional application No. 60/728,292, filed on Oct. 19, 2005, provisional application No. 60/751,196, filed on Dec. 16, 2005, provisional application No. 60/433,017, filed on Dec. 13, 2002, provisional application No. 61/207,890, filed on Feb. 13, 2009, provisional application No. 61/266,356, filed on Dec. 3, 2009, provisional application No. 61/292,656, filed on Jan. 6, 2010, provisional application No. 61/322,997, filed on Apr. 12, 2010, provisional application No. 61/323,952, filed on Apr. 14, 2010.

(56) References Cited

U.S. PATENT DOCUMENTS

| | | |
|---|---|---|
| 5,112,954 A | 5/1992 | Abrams et al. |
| 5,185,254 A | 2/1993 | Linnenbach |
| 5,530,101 A | 6/1996 | Queen et al. |
| 5,693,762 A | 12/1997 | Queen et al. |
| 5,708,146 A | 1/1998 | Willner et al. |
| 5,776,427 A | 7/1998 | Thorpe et al. |
| 5,824,701 A | 10/1998 | Greenwald et al. |
| 5,840,854 A | 11/1998 | Hellstrom et al. |
| 5,859,205 A | 1/1999 | Adair et al. |
| 6,017,514 A | 1/2000 | Epstein et al. |
| 6,120,995 A | 9/2000 | Waldman et al. |
| 6,156,754 A | 12/2000 | Lerchen et al. |
| 6,176,842 B1 | 1/2001 | Tachibana et al. |
| 6,180,377 B1 | 1/2001 | Morgan et al. |
| 6,214,345 B1 | 4/2001 | Firestone et al. |
| 6,261,537 B1 | 7/2001 | Klaveness et al. |
| 6,342,219 B1 | 1/2002 | Thorpe et al. |
| 6,558,669 B1 | 5/2003 | Govindan et al. |
| 6,632,926 B1 | 10/2003 | Chen et al. |
| 6,653,104 B2 | 11/2003 | Goldenberg et al. |
| 6,716,821 B2 | 4/2004 | Zhao et al. |
| 6,962,702 B2 | 11/2005 | Hansen et al. |
| 6,989,140 B2 | 1/2006 | Tidmarsh et al. |
| 7,115,261 B1 | 10/2006 | Lode et al. |
| 7,122,636 B1 | 10/2006 | Hsei et al. |
| 7,238,785 B2 | 7/2007 | Govindan et al. |
| 7,288,249 B2 | 10/2007 | Carter et al. |
| 7,312,318 B2 | 12/2007 | Hansen et al. |
| 7,387,772 B1 | 6/2008 | Hansen et al. |
| 7,420,040 B2 | 9/2008 | Young et al. |
| 7,420,041 B2 | 9/2008 | Young et al. |
| 8,309,094 B2 | 11/2012 | Gerber et al. |
| 8,715,662 B2 | 5/2014 | Alberti |
| 2001/0034363 A1 | 10/2001 | Li et al. |
| 2002/0041847 A1 | 4/2002 | Goldenberg et al. |
| 2003/0096249 A1 | 5/2003 | Westphal et al. |
| 2003/0133972 A1 | 7/2003 | Danthi et al. |
| 2003/0162709 A1 | 8/2003 | Rossi et al. |
| 2003/0198595 A1 | 10/2003 | Goldenberg et al. |
| 2004/0001825 A1 | 1/2004 | Govindan et al. |
| 2005/0002945 A1 | 1/2005 | McBride et al. |
| 2005/0053606 A1* | 3/2005 | Kufe et al. ............... 424/155.1 |
| 2006/0142506 A1 | 6/2006 | Breitenkamp et al. |
| 2007/0086942 A1 | 4/2007 | Chang et al. |
| 2008/0166363 A1 | 7/2008 | Govindan et al. |
| 2012/0237518 A1 | 9/2012 | Yamaguchi et al. |
| 2013/0089872 A1 | 4/2013 | Nakamura et al. |
| 2013/0122020 A1 | 5/2013 | Liu et al. |

FOREIGN PATENT DOCUMENTS

| | | |
|---|---|---|
| EP | 0306943 | 3/1989 |
| WO | 9714796 | 4/1997 |
| WO | 98/12227 | 3/1998 |
| WO | 98/42378 | 10/1998 |
| WO | 00/69914 | 11/2000 |
| WO | 0076551 | 12/2000 |
| WO | 0124763 | 4/2001 |
| WO | 2003106495 | 12/2003 |
| WO | 2004054622 | 7/2004 |

OTHER PUBLICATIONS

Wang et al. (Int. J. Cancer, vol. 121, 2716-2722, 2007).*
Stein et al. (Cancer Research, vol. 50, pp. 1330-1336, 1990).*
Alberts et al., Molecular Biology of the Cell, 3rd Ed., pp. 1216-1218, Garland Publishing, Inc. (1994).
Basu et al., "The epithelial/carcinoma antigen EGP-1, recognized by monoclonal antibody RS7-3G11, is phosphorylated on serine 303" Int. J. Cancer 62(4):472-479 (1995).
Bendig et al., "Humanization of Rodent Monoclonal Antibodies by CDR Grafting" Methods: A Companion to Methods in Enzymology 8:83-93-93 (1995).
Bennouna et al., "Therapeutic strategies for colorectal cancer in Europe and the United States: focus on chemotherapy for advanced colorectal cancer" Int. J. Clin. Oncol. (2002) 7:236-244.
Cao et al., "Bispecific Antibodies as Novel Bioconjugates" Bioconj. Chem. Nov.-Dec. 1998;9(6):635-44.
Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Chari et al., "Immunoconjugates Containing Novel Maytansinoids: Promising Anticancer Drugs" Cancer Res. Jan. 1, 1992;52(1):127-31.
Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Hatzakis et al., "Synthesis and single enzyme activity of a clicked lipase-BSA hetero-dimer" Chem. Commun., 2006, 2012-2014.
Heindel et al., "A Novel Heterobifunctional Linker for Formyl to Thiol Coupling" Bioconjugate Chem. 1991, 2, 427-430.
Huang et al., "The Rana catesbeiana rcr Gene Encoding a Cytotoxic Ribonuclease" J. Biol. Chem. 273(11):6395-6401 (1998).
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Leung et al., "Chimerization of LL2, a Rapidly Internalizing Antibody Specific for B Cell Lymphoma" Hybridoma 13(6):469-476 (1994).
Miller et al., "Development of Taxoids with Enhanced Toxicity and Solubility" Poster Presentation, 224th ACS Nat. Meeting, Aug. 18-22, 2002, Boston, MA.
Moon et al., "Antibody Conjugates of 7-Ethyl-10-hydroxycamptothecin (SN-38) for Targeted Cancer Chemotherapy" J. Med. Chem. 2008, 51, 6916-6926.

(56) References Cited

OTHER PUBLICATIONS

Morrison et al., "Chimeric human antibody molecules: Mouse antigen-binding domains with human constant region domains" Proc. Natl. Acad. Sci, USA 81:6851-6855 (1984).
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W. Fundamental Immunology, 3rd Ed., p. 242; pp. 292-295, Raven Press, New York (1993).
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Qu et al., "Humanization of Immu31, an α-Fetoprotein-specific Antibody" Clin. Cancer Res. 5(10 Suppl):3094s-3100s (1999).
Reddy et al., "Elimination of Fc Receptor-Dependent Effector Functions of a Modified IgG4 Monoclonal Antibody to Human CD4", J. Immunol. 164:1925-1933 (2000).
Ripani et al., "Human Trop-2 is a tumor-associated calcium signal transducer", Int J Cancer. May 29, 1998;76(5):671-6.
Rowlinson-Busza et al., "Targeted delivery of biologic and other antineoplastic agents" Curr. Opin. Oncol. Dec. 1992;4(6):1142-1148.
Rudikoff et al., "Single amino acid substitution altering antigen-binding specificity" Proc. Natl. Acad. Sci. USA 79:1979-1983 (1982).
Schoonjans et al., "FAB chains as an Efficient Heterodimerization Scaffold for the Production of Recombinant Bispecific and Trispecific Antibody Derivatives" J. Immunol. 165(12):7050-7057 (2000).
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Sharkey et al., "Epratuzumab-SN-38: a new antibody-drug conjugate for the therapy of hematologic malignancies", Mol Cancer Ther. Jan. 2012;11(1):224-34.
Shih et al., "In Vitro and in Vivo Reactivity of an Internalizing Antibody, RS7, with Human Breast Cancer" Cancer Res. 55(23 Suppl.):5857s-5863s (1995).
Shih et al., "The Processing and Fate of Antibodies and Their Radiolabels Bound to the Surface of Tumor Cells in Vitro: A Comparison of Nine Radiolabels" J. Nucl. Med. 1994; 35:899-908.
Stein et al., "Therapy of a Breast Cancer Xenograft Using Humanized RS7 Labeled with Residualizing Iodine" Proc. Am. Assoc. Cancer Res. vol. 43, pp. 88-89, Mar. 2002 (Abstract).
Stein et al., "Comparative Biodistribution and Radioimmunotherapy of Monoclonal Antibody RS7 and its F(ab')2 in Nude Mice Bearing Human Tumor Xenografts" Cancer 73:816-823 (1994).
Stein et al., "Effects of Radiolabeling Monoclonal Antibodies with a Residualizing Iodine Radiolabel on the Accretion of Radioisotope in Tumors" Cancer Res. 55(14):3132-3139 (1995).
Stein et al., "Specificity and properties of MAb RS7-3G11 and the antigen defined by this pancarcinoma monoclonal antibody" Int. J. Cancer 55(6):938-946 (1993).
Stein et al., "Characterization of cluster 13: the epithelial/carcinoma antigen recognized by MAb RS7" Int. J. Cancer 57(S8):98-102 (1994).
Stein et al., "Murine Monoclonal Antibodies Raised against Human Non-Small Cell Carcinoma of the Lung: Specificity and Tumor Targeting" Cancer Res. 50(4):1330-1336 (1990).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).

Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Walker et al., "Synthesis of an Immunoconjugate of Camptothecin" Bioorg. Med. Chem. Lett. 12(2):217-219 (2002).
Wang et al., "Diagnostic value of mucins (MUC1, MUC2 and MUC5AC) expression profile in endoscopic ultrasound-guided fine-needle aspiration specimens of the pancreas", Int J Cancer. Dec. 15, 2007;121(12):2716-22.
Arlen et al., "The use of specific monoclonal antibodies to target immunogenic tumor membrane proteins in patients with recurrent pancreatic and colon cancer", Curr Drug Deily. Jan. 2012;9(1):52-6.
Bamrungphon et al. "A new mucin antibody/enzyme-linked lectin-sandwich assay of serum MUC5AC mucin for the diagnosis of cholangiocarcinoma", Cancer Lett. Mar. 18, 2007;247(2):301-8.
Brennan et al., "Novel agents for the treatment of pancreatic cancer", JOP. Mar. 10, 2014;15(2):110-3.
Bu et al. "Altered expression of MUC2 and MUC5AC in progression of colorectal carcinoma", World J Gastroenterol. Aug. 28, 2010;16(32):4089-94.
Cardillo et al., "Therapeutic Advantage of 90Yttrium-versus 131Iodine-labeled PAM4 Antibody in Experimental Pancreatic Cancer" Clin. Cancer Res. 7(10):3186-3192, Oct. 2001.
Cardillo et al., "Combined Gemcitabine and Radioimmunotherapy for the Treatment of Pancreatic Cancer" Int. J. Cancer: 97(3):386-392 (2002).
Clark et al., "Antibody humanization: a case of the Emeror's new clothes?" Immunol. Today 21(8):397-402 (2000).
Daniel et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity is Drastically Influenced by the Nature of the Protein Carrier" Virology 202, 540-549 (1994).
Dall'Acqua et al., "Antibody Engineering" Curr. Opin. Struct. Biol., Aug. 1998; 8(4):443-50.
Emery et al., "Humanised monoclonal antibodies for therapeutic applications" Exp. Opin. Invest. Drugs (1994) 3(3):241-251.
Forgue-Lafitte et al., "Abnormal expression of M1/MUC5AC mucin in distal colon of patients with diverticulitis, ulcerative colitis and cancer", Int J Cancer. Oct. 1, 2007;121(7):1543-9.
Gold et al., "Radioimmunotherapy of Experimental Pancreatic Cancer with 131I-Labeled Monoclonal Antibody PAM4" Int. J. Cancer: 71(4):660-667 (1997).
Gold et al., "Chimerization and CDR-grafted humanization of PAM4, a murine monoclonal anti-pancreatic cancer antibody" Proc AACR 1993; 34:480, abstract 2866.
Gold et al., "Characterization of Monoclonal Antibody PAM4 Reactive with a pancreatic Cancer Mucin" Int. J. Cancer 57(2): 204-210 (1994).
Gold et al., "Localization of pancreatic cancer with radiolabeled monoclonal antibody PAM4" Crit. Rev. Oncol. Hematol. Jul.-Aug. 2001;39(1-2):147-154.
Gold et al., "PAM4-reactive MUC1 is a biomarker for early pancreatic adenocarcinoma", Clin Cancer Res. Dec. 15, 2007;13(24):7380-7.
Greenspan et al., "Defining epitopes: Its not as easy as it seems" Nat. Biotech. 17:936-937 (1999).
Haab et al., "Glycosylation variants of mucins and CEACAMs as candidate biomarkers for the diagnosis of pancreatic cystic neoplasms", Ann Surg. May 2010;251(5):937-45.
Han et al., "Combination of MUC5ac and WT-1 immunohistochemistry is useful in distinguishing pancreatic ductal carcinoma from ovarian serous carcinoma in effusion cytology", Diagn Cytopathol. May 2010;38(5):333-6.
Ho et al., "Antisense Oligonucleaotides as Therapeutics for Malignant Diseases" Semin. Oncol. 24(2):187-202 (1997).
Ho et al., "Methylation status of promoters and expression of MUC2 and MUC5AC mucins in pancreatic cancer cells", Int J Oncol. Feb. 2003;22(2):273-9.

(56) References Cited

OTHER PUBLICATIONS

Ho et al., "Secretion of MUC5AC mucin from pancreatic cancer cells in response to forskolin and VIP", Biochem Biophys Res Commun. Jun. 14, 2002;294(3):680-6.
Hoshi et al., "Tumor-associated MUC5AC stimulates in vivo tumorigenicity of human pancreatic cancer", Int J Oncol. Mar. 2011;38(3):619-27.
Jones, DT "Critically assessing the state-of-the-art in protein structure prediction" Pharmacogenomics J.; 1:126-134, 2001.
Kanno et al., "The expression of MUC4 and MUC5AC is related to the biologic malignancy of intraductal papillary mucinous neoplasms of the pancreas", Pancreas. Nov. 2006;33(4):391-6.
Karacay et al., "A Pretargeting Bispecific Antibody Method for Improved Imaging and Therapy of Pancreatic Cancer" J. Nucl. Med., vol. 43, No. 5(Suppl.), May 2002, p. 369P, No. 1484.
Kipriyanov et al., "Generation of Recombinant Antibodies" Mol. Biotechnol., vol. 12, Sep. 1999; pp. 173-201.
Klivenyi et al., "Gallium-68 Chelate Imaging of Human Colon Carcinoma Xenografts Pretargeted with Bispecific Anti-CD44V6/Anti-Gallium Chelate Antibodies" J. Nucl. Med. 39(10): pp. 1769-1776, Oct. 1998.
Kunze et al., "Tumor-associated neoexpression of the pS2 peptide and MUC5AC mucin in primary adenocarcinomas and signet ring cell carcinomas of the urinary bladder", Histol Histopathol. May 2008;23(5):539-48.
Linnenbach et al., "Sequence investigation of the major gastrointestinal tumor-associated antigen gene family, GA733", Proc Natl Acad Sci U S A. Jan. 1989;86(1):27-31.
Luka et al., "Development of a serum biomarker assay that differentiates tumor-associated MUC5AC (NPC-1C Antigen) from normal MUC5AC", J Biomed Biotechnol. 2011;2011:934757.
Mariani et al., "Initial Tumor Targeting, Biodistribution, and Pharmacokinetic Evaluation of the Monoclonal Antibody PAM4 in Patients with Pancreatic Cancer" Cancer Res. Suppl. 55, 5911s-5915s, Dec. 1, 1995.
Maurin et al. "Progression of tumors arising from large ACF is associated with the MUC5AC expression during rat colon MNNG carcinogenis", Int J Cancer. Feb. 1, 2007;120(3):477-83.
Patel et al., "Anti-tumor activity of a novel monoclonal antibody, NPC-1C, optimized for recognition of tumor antigen MUC5AC variant in preclinical models", Cancer Immunol Immunother. Jun. 2013;62(6):1011-9.
Price et al., "Summary Report on the ISOBM TD-4 Workshop: Analysis of 56 Monoclonal Antibodies against the MUC1 Mucin" Tumor Biol. 1998, 19(Suppl. 1):1-20.
Reis et al. "Immunohistochemical study of MUC5AC expression in human gastric carcinomas using a novel monoclonal antibody", Int J Cancer Feb. 20, 1997;74(1):112-21.
Schuhmacher et al., "Pretargeting of human mammary carcinoma xenografts with bispecific anti-MUC1/anti-Ga chelate antibodies and immunoscintigraphy with PET" Nucl. Med. Biol. 28 (2001) 821-828.
Skolnick et al., "From genes to protein structure and function: novel applications of computational approaches in the genomic era" Trends Biotechnol. 2000; 18:34-39.
Silsirivanit et al., "A novel serum carbohydrate marker on mucin 5AC: values for diagnostic and prognostic indicators for cholangiocarcinoma", Cancer. Aug. 1, 2011;117(15)3393-403.
Tosatto et al., "Large-Scale Prediction of Protein Structure and Function from Sequence" Curr. Pharm. Des., 12, 2006, 2067-2086.
Walker et al., "Improved Cellular Delivery of Antisense Oligonucleotides Using Transferrin Receptor Antibody-Oligonucleotide Conjugates" Pharm. Res., 12(10):1548-53, (1995).
Wongkham et al. "Serum MUC5AC mucin as a potential marker for cholangiocarcinoma", Cancer Lett. May 30, 2003;195(1):93-9.
Alisauskus et al., "Initial studies of monoclonal antibody PAM4 targeting to xenografted orthotopic pancreatic cancer", Cancer Res. Dec. 1, 1995;55(23 Suppl):5743s-5748s.
Baeuerle et al., "EpCAM (CD326) finding its role in cancer", Br J Cancer. Feb. 12, 2007;96(3):417-23.

Cardillo et al., "Improved targeting of pancreatic cancer: experimental studies of a new bispecific antibody, pretargeting enhancement system for immunoscintigraphy", Clin Cancer Res. May 15, 2004;10(10):3552-61.
Chopra et al., "125I-Labeled trivalent, bispecific monoclonal antibody construct TF10 that targets mucin-1 and is reactive against a histamine-succinyl-glycine hapten IMP-288", Molecular Imaging and Contrast Agent Database (MICAD) [Internet]. Bethesda (MD): National Center for Biotechnology Information (US); 2004-2013. Jun. 29, 2011 [updated Aug. 25, 2011].
Chopra et al., "111In/125/131I-Labeled anti-mucin-1 murine, chimeric or humanized antibody hPAM4", Molecular Imaging and Contrast Agent Database (MICAD) [Internet]. Bethesda (MD): National Center for Biotechnology Information (US); 2004-2013. Jun. 16, 2011 [updated Jul. 26, 2011].
Eguia et al., "Early detection of pancreatic cancer", JOP. Mar. 10, 2012;13(2):131-4.
Glazer et al., "Noninvasive radiofrequency field destruction of pancreatic adenocarcinoma xenografts treated with targeted gold nanoparticles", Clin Cancer Res. Dec. 1, 2010;16(23):5712-21.
Gold et al., "Mapping PAM4 (clivatuzumab), a monoclonal antibody in clinical trials for early detection and therapy of pancreatic ductal adenocarcinoma, to MUC5AC mucin", Mol Cancer. Nov. 20, 2013;12(1):143.
Gold et al., "PAM4 enzyme immunoassay alone and in combination with CA 19-9 for the detection of pancreatic adenocarcinoma", Cancer. Feb. 1, 2013;119(3):522-8.
Gold et al., "Combined 90Yttrium-Dota-labeled PAM4 antibody radioimmunotherapy and gemcitabine radiosensitization for the treatment of a human pancreatic cancer xenograft", Int J Cancer. Apr. 20, 2004;109(4):618-26.
Gold et al., "Low-dose radioimmunotherapy ((90)Y-PAM4) combined with gemcitabine for the treatment of experimental pancreatic cancer", Clin Cancer Res. Sep. 1, 2003;9(10 Pt 2):3929S-37S.
Gold et al., "Targeting of xenografted pancreatic cancer with a new monoclonal antibody, PAM4", Cancer Res. Mar. 1, 1995;55(5):1105-10.
Gold et al., "Detection of early-stage pancreatic adenocarcinoma", Cancer Epidemiol Biomarkers Prev. Nov. 2010;19(11):2786-94.
Gold et al., "A novel bispecific, trivalent antibody construct for targeting pancreatic carcinoma", Cancer Res. Jun. 15, 2008;68(12):4819-26.
Gold et al., "New MUC1 serum immunoassay differentiates pancreatic cancer from pancreatitis", J Clin Oncol. Jan. 10, 2006;24(2):252-8.
Han et al., "The role of PAM4 in the management of pancreatic cancer: diagnosis, radioimmunodetection, and radioimmunotherapy", J Immunol Res. 2014;2014:268479.
Hoimes et al., "Biomarkers for early detection and screening in pancreatic cancer", Highlights from the 45th ASCO annual meeting. Orlando, FL, USA. May 29-Jun. 2, 2009, JOP. Jul. 6, 2009;10(4):352-6.
Karacay et al., , "Pretargeted radioimmunotherapy of pancreatic cancer xenografts: TF10-90Y-IMP-288 alone and combined with gemcitabine", J Nucl Med. Dec. 2009;50(12):2008-16.
Lipinski et al., "Human trophoblast cell-surface antigens defined by monoclonal antibodies", Proc Natl Acad Sci U S A. Aug. 1981;78(8):5147-50.
Liu et al., "Identification of PAM4 (clivatuzumab)-reactive epitope on MUC5AC: A promising biomarker and therapeutic target for pancreatic cancer", Oncotarget. Feb. 28, 2015;6(6):4274-85.
Schmidt, C., "Early detection tools for pancreatic cancer", J Natl Cancer Inst. Aug. 8, 2012;104(15):1117-8.
Shi et al., "Differentiation of pancreatic ductal adenocarcinoma from chronic pancreatitis by PAM4 immunohistochemistry", Arch Pathol Lab Med. Feb. 2014;138(2):220-8.
Goldenberg et al., "Trop-2 is a novel target for solid cancer therapy with sacituzumab govitecan (IMMU-132), an antibody-drug conjugate (ADC)", Oncotarget Jun. 18, 2015. [Epub ahead of print].

* cited by examiner

A

B

COMBINING RADIOIMMUNOTHERAPY AND ANTIBODY-DRUG CONJUGATES FOR IMPROVED CANCER THERAPY

RELATED APPLICATIONS

This application is a divisional of U.S. patent application Ser. No. 14/029,165, filed Sep. 17, 2013, which was a divisional of U.S. patent application Ser. No. 13/855,213, filed Apr. 2, 2013 (now issued U.S. Pat. No. 8,586,050), which was a divisional of U.S. patent application Ser. No. 12/957,655 (now issued U.S. Pat. No. 8,435,529), filed Dec. 1, 2010, which was a continuation-in-part of U.S. patent application Ser. No. 12/537,803 (now issued U.S. Pat. No. 8,491,896), filed Aug. 7, 2009; which was a continuation-in-part of U.S. patent application Ser. No. 11/849,791 (now abandoned), filed Sep. 4, 2007, which was a divisional of U.S. patent application Ser. No. 10/461,885 (now issued U.S. Pat. No. 7,282,567), filed Jun. 16, 2003. Those applications claimed the benefit under 35 U.S.C. 119(e) of U.S. Provisional Patent Application Ser. Nos. 60/388,314, filed Jun. 14, 2002; 61/087,463, filed Aug. 8, 2008; and 61/144,227, filed Jan. 13, 2009. Ser. No. 12/957,655 is a continuation-in-part of U.S. patent application Ser. No. 12/389,503 (now issued U.S. Pat. No. 8,084,583), filed Feb. 20, 2009, which was a continuation of U.S. patent application Ser. No. 11/745,896 (now issued U.S. Pat. No. 7,517,964), filed May 8, 2007, which was a divisional of U.S. patent application Ser. No. 10/377,121 (now issued U.S. Pat. No. 7,238,785), filed Mar. 3, 2003, which claimed the benefit of U.S. Provisional Patent Application Ser. No. 60/360,229, filed Mar. 1, 2002. Ser. No. 12/957,655 is a continuation-in-part of U.S. patent application Ser. No. 12/629,404 (now issued U.S. Pat. No. 7,999,083), filed Dec. 2, 2009; which was a continuation of U.S. patent application Ser. No. 12/026,811 (now issued U.S. Pat. No. 7,591,994); which was a continuation-in-part of U.S. patent application Ser. No. 11/388,032 (now issued U.S. Pat. No. 8,877,901), filed Mar. 23, 2006; which was a continuation-in-part of U.S. patent application Ser. No. 10/734,589 (now issued U.S. Pat. No. 7,585,491). Those applications claimed the benefit of U.S. Provisional Patent Application Ser. Nos. 60/688,603, filed Apr. 6, 2005; 60/728,292, filed Oct. 19, 2005; 60/751,196, filed Dec. 16, 2005; 60/433,017, filed Dec. 13, 2002; and 61/207,890, filed Feb. 13, 2009. This application claims the benefit under 35 U.S.C. 119(e) of U.S. Provisional Patent Application Ser. Nos. 61/266,356, filed Dec. 3, 2009; 61/292,656, filed Jan. 6, 2010; 61/322,997, filed Apr. 12, 2010; and 61/323,952, filed Apr. 14, 2010. The text of each priority application cited above is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 29, 2010, is named IMM324US.txt and is 21,844 bytes in size.

BACKGROUND OF THE INVENTION

1. Field of the Invention
This invention relates to combined therapy of cancer cells using radiolabeled antibodies (RAIT) and antibodies conjugated to drug moieties (ADC). In preferred embodiments, the combination of RAIT and ADC exhibits a synergistic effect and is more effective to induce cancer cell death than either RAIT or ADC alone, or the sum of the effects of RAIT and ADC administered individually. In more preferred embodiments, the combination RAIT and ADC is effective to treat pancreatic cancer. In most preferred embodiments, the labeled antibodies or antibody fragments may comprise a PAM4 (anti-pancreatic cancer mucin) antibody and an RS7 (anti-Trop-2) antibody. However, the skilled artisan will realize that other combinations of antibodies or fragments thereof may be utilized and other forms of cancer may be treated.

2. Related Art
Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

The most common symptoms of pancreatic cancer include jaundice, abdominal pain, and weight loss, which, together with other presenting factors, are nonspecific in nature. Thus, diagnosing pancreatic cancer at an early stage of tumor growth is often difficult and requires extensive diagnostic work-up, often times including exploratory surgery. Endoscopic ultrasonography and computed tomography are the best noninvasive means available today for diagnosis of pancreatic cancer. However, reliable detection of small tumors, as well as differentiation of pancreatic cancer from focal pancreatitis, is difficult. The vast majority of patients with pancreatic cancer are presently diagnosed at a late stage when the tumor has already extended outside of the capsule to invade surrounding organs and/or has metastasized extensively. Gold et al., Crit. Rev. Oncology/Hematology, 39:147-54 (2001). Late detection of the disease is common, and early pancreatic cancer diagnosis is rare in the clinical setting.

Current treatment procedures available for pancreatic cancer have not led to a cure, or to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%.

Antibodies, in particular monoclonal antibodies (MAbs) and engineered antibodies or antibody fragments, have been widely tested and shown to be of value in detection and treatment of various human disorders, including cancers, autoimmune diseases, infectious diseases, inflammatory diseases, and cardiovascular diseases [Filpula and McGuire, Exp. Opin. Ther. Patents (1999) 9: 231-245]. The clinical utility of an antibody or an antibody-derived agent is primarily dependent on its ability to bind to a specific targeted antigen associated with a particular disorder. Selectivity is valuable for delivering a therapeutic agent, such as drugs, toxins, cytokines, hormones, hormone antagonists, enzymes, enzyme inhibitors, inhibitory oligonucleotides (e.g., RNAi, siRNA), immunomodulators, radionuclides, anti-angiogenic agents or pro-apoptotic agents, to a targeted tumor. Radiolabeled antibodies have been used with some success in numerous malignancies, including ovarian cancer, colon cancer, medullary thyroid cancer, and lymphomas.

While various antibodies have been approved for human therapeutic use, including alemtuzumab, bevacizumab, cetuximab, gemtuzumab, ibritumomab, panitumumab, rituximab, tositumomab and trastuzumab, a need exists in the field for more efficacious antibody-based therapies for difficult to treat cancers, such as pancreatic cancer.

SUMMARY

In various embodiments, the present invention concerns combination therapy with radiolabeled antibodies and drug-conjugated antibodies. The combination therapy may be of use for treatment of cancers for which standard therapies are not effective, such as pancreatic cancer. In preferred embodiments the combination of radiolabeled and drug-conjugated antibodies is more efficacious than either radiolabeled antibody alone, drug-conjugated antibody alone, or the sum of the effects of radiolabeled and drug-conjugated antibody administered individually. In specific embodiments, the antibodies may bind respectively to human pancreatic cancer mucin and to EGP-1 (Trop-2). However, many antibodies against tumor-associated antigens (TAAs) are known and the skilled artisan will realize that various combinations of anti-TAA antibodies may be of use.

Preferably the antibodies of use bind specifically to cancer cells, with little or no binding to normal or non-neoplastic cells. More preferably, the antibodies bind to the earliest stages of cancer, such as PanIN-1A and 1B and PanIN-2 in the case of pancreatic cancer. Most preferably, the antibodies bind to 80 to 90% or more of human invasive pancreatic adenocarcinoma, intraductal papillary mucinous neoplasia, PanIN-1A, PanIN-1B and PanIN-2 lesions, but not to normal human pancreatic tissue.

In a specific embodiment, the radiolabeled antibody may be a humanized PAM4 antibody (see, e.g., U.S. Pat. No. 7,282,567, incorporated herein by reference in its entirety), comprising the light complementarity determining region (CDR) sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6). As discussed below, a number of therapeutic radionuclides of use for cancer treatment are known and any such known radionuclide may be conjugated to the antibody of interest. In a more preferred embodiment, the radiolabeled antibody is $^{90}$Y-hPAM4 (clivatuzumab tetraxetan).

In another specific embodiment, the drug-conjugated antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:7); CDR2 (SASYRYT, SEQ ID NO:8); and CDR3 (QQHYITPLT, SEQ ID NO:9) and the heavy chain CDR sequences CDR1 (NYGMN, SEQ ID NO:10); CDR2 (WINTYTGEPTYTDDFKG, SEQ ID NO:11) and CDR3 (GGFGSSYWYFDV, SEQ ID NO:12). As discussed below, a number of chemotherapeutic drugs of use for cancer treatment are known and any such known drug may be conjugated to the antibody of interest. In a more preferred embodiment, the drug-conjugated antibody is SN-38-hRS7.

In alternative embodiments, the antibodies may be murine, chimeric, humanized or human antibodies that bind to the same antigenic determinant (epitope) as a PAM4 antibody comprising the light complementarity determining region (CDR) sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6); or that bind to the same epitope as an RS7 antibody comprising the light chain CDR sequences CDR1 (KASQDVSIAVA, SEQ ID NO:7); CDR2 (SASYRYT, SEQ ID NO:8); and CDR3 (QQHYITPLT, SEQ ID NO:9) and the heavy chain CDR sequences CDR1 (NYGMN, SEQ ID NO:10); CDR2 (WINTYTGEPTYTDDFKG, SEQ ID NO:11) and CDR3 (GGFGSSYWYFDV, SEQ ID NO:12). Antibodies that bind to the same antigenic determinant may be identified by a variety of techniques known in the art, such as by competitive binding studies.

In preferred embodiments, the radiolabeled antibody and drug-conjugated antibody are administered as separate antibody moieties, either sequentially or concurrently. However, in alternative embodiments, the radiolabeled antibody and drug-conjugated antibody, or fragments thereof, may be administered as a bispecific antibody. In preferred alternative embodiments, the bispecific antibody may be produced by the dock-and-lock (DNL) technique, as discussed in more detail below.

Although in preferred embodiments, the antibodies or antibody fragments are conjugated respectively to a radionuclide and a chemotherapeutic drug, the skilled artisan will realize that other anticancer therapeutic agents are known in the art and may potentially be substituted for, or used in addition to, the subject radionuclide and/or drug. Other known therapeutic agents include toxins, immunomodulators (such as cytokines, lymphokines, chemokines, growth factors and tumor necrosis factors), hormones, hormone antagonists, enzymes, oligonucleotides (such as siRNA or RNAi), photoactive therapeutic agents, anti-angiogenic agents and pro-apoptotic agents. The therapeutic agents may comprise one or more copies of the same therapeutic agent or else combinations of different therapeutic agents. The therapeutic agents may be conjugated to the subject antibodies or separately administered before, concurrently with or after the subject antibodies.

In a preferred embodiment, the therapeutic agent is a cytotoxic agent, such as a drug or a toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate, CPT-11, and a combination thereof.

In another preferred embodiment, the therapeutic agent is a toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin and combinations thereof. Or an immunomodulator selected from the group consisting of a cytokine, a stem cell growth factor, a lymphotoxin, a hematopoietic factor, a colony stimulating factor (CSF), an interferon (IFN), erythropoietin, thrombopoietin and a combinations thereof.

In other preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. In other embodiments the therapeutic agent is a photoactive therapeutic agent selected from the group consisting of chromogens and dyes.

Alternatively, the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

In other alternative embodiments, anti-TAA antibodies other than PAM4 and/or RS7 may be utilized. Preferably, the antibody or fragment thereof binds to a tumor-associated antigen selected from the group consisting of CA19.9, DUPAN2, SPAN1, Nd2, B72.3, CC49, CEA (CEACAM5), CEACAM6, Le$^a$, the Lewis antigen Le(y), CSAp, insulin-like growth factor (ILGF), epithelial glycoprotein-1 (EGP-1), epithelial glycoprotein-2 (EGP-2), CD80, placental growth factor (PlGF), carbonic anhydrase IX, tenascin, IL-6, HLA-DR, CD40, CD74 (e.g., milatuzumab), CD138 (syndecan-1), MUC-1, MUC-2, MUC-3, MUC-4, MUC-5ac, MUC-16, MUC-17, TAG-72, EGFR, platelet-derived growth factor (PDGF), angiogenesis factors (e.g., VEGF and PlGF), products of oncogenes (e.g., bcl-2, Kras, p53), cMET, HER2/neu, and antigens associated with gastric cancer and colorectal cancer.

DETAILED DESCRIPTION

Definitions

Figure 1:
FIG. 1. PET/CT fusion images for a patient with inoperable metastatic pancreatic cancer treated with fractionated $^{90}$Y-hPAM4 plus gemcitabine, before therapy (left side) and post-therapy (right side). The circle indicates the location of the primary lesion, which shows a significant decrease in PET/CT intensity following therapy.
Figure 1:

Unless otherwise specified, "a" or "an" means one or more.

As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, Fab', Fab, Fv, sFv and the like. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples section of which are incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

A multispecific antibody is an antibody that can bind simultaneously to at least two targets that are of different structure, e.g., two different antigens, two different epitopes on the same antigen, or a hapten and/or an antigen or epitope. Multispecific, multivalent antibodies are constructs that have more than one binding site, and the binding sites are of different specificity.

A bispecific antibody is an antibody that can bind simultaneously to two different targets. Bispecific antibodies (bsAb) and bispecific antibody fragments (bsFab) may have at least one arm that specifically binds to, for example, a tumor-associated antigen and at least one other arm that specifically binds to a targetable conjugate that bears a therapeutic or diagnostic agent. A variety of bispecific fusion proteins can be produced using molecular engineering.

PAM4 Antibody

Various embodiments of the invention concern antibodies that react with very high selectivity with pancreatic cancer as opposed to normal or benign pancreatic tissues. The anti-pancreatic cancer antibodies and fragments thereof are preferably raised against a crude mucin preparation from a tumor of the human pancreas, although partially purified or even purified mucins may be utilized. A non-limiting example of such antibodies is the PAM4 antibody.

The murine PAM4 (mPAM4) antibody was developed by employing pancreatic cancer mucin derived from the xenografted RIP-1 human pancreatic carcinoma as immunogen. (Gold et al., Int. J. Cancer, 57:204-210, 1994.) Antibody cross-reactivity and immunohistochemical staining studies indicate that the PAM4 antibody recognizes a unique and novel epitope on a target pancreatic cancer antigen. Immunohistochemical staining studies, (see, e.g., U.S. Pat. No. 7,282, 567), have shown that the PAM4 MAb binds to an antigen expressed by breast, pancreas and other cancer cells, with limited binding to normal human tissue; however, the highest expression is usually by pancreatic cancer cells. Thus, the PAM4 antibodies are relatively specific to pancreatic cancer and preferentially bind pancreatic cancer cells. The PAM4 antibody is reactive with a target epitope which can be internalized. This epitope is expressed primarily by antigens associated with pancreatic cancer and not with focal pancreatitis or normal pancreatic tissue. Localization and therapy studies using a radiolabeled PAM4 MAb in animal models have demonstrated tumor targeting and therapeutic efficacy (Id.).

The PAM4 antibody exhibits several properties which make it a good candidate for clinical diagnostic and therapeutic applications. The PAM4 antibody apparently recognizes an epitope of a pancreatic cancer antigen that is distinct from the epitopes recognized by non-PAM4 anti-pancreatic cancer antibodies (CA19.9, DUPAN2, SPAN1, Nd2, CEACAM5, CEACAM6, B72.3, anti-Le$^a$, and other anti-Lewis antigens) (Id.). Antibodies suitable for use in combination or conjunction with PAM4 antibody include, for example, CA19.9, DUPAN2, SPAN1, Nd2, B72.3, CC49, anti-CEACAM5, anti-CEACAM6, anti-Le$^a$, anti-HLA-DR, anti-CD40, anti-CD74, anti-CD138, and antibodies defined by the Lewis antigen Le(y), or antibodies against colon-specific antigen-p (CSAp), MUC-1, MUC-2, MUC-3, MUC-4, MUC-5ac, MUC-16, MUC-17, EGP-1, EGP-2, HER2/neu, EGFR, angiogenesis factors (e.g., VEGF and PlGF), insulin-like growth factor (ILGF), tenascin, platelet-derived growth factor, and IL-6, as well as products of oncogenes (bcl-2, Kras, p53), cMET, and antibodies against tumor necrosis substances, such as described in patents by Epstein et al. (U.S. Pat. Nos. 6,071,491, 6,017,514, 5,019,368 and 5,882,626). Such antibodies would be useful for complementing PAM4 antibody reactivity with pancreatic cancer. These and other therapeutic agents could act synergistically with PAM4 antibody, when administered before, together with or after administration of PAM4 antibody.

Preferred embodiments may involve the use of a humanized PAM4 antibody. Because non-human monoclonal antibodies can be recognized by the human host as a foreign protein, and repeated injections can lead to harmful hypersensitivity reactions, humanization of a murine antibody sequences can reduce the adverse immune response that patients may experience. For murine-based monoclonal antibodies, this is often referred to as a Human Anti-Mouse Antibody (HAMA) response. Preferably some human residues in the framework regions of the humanized PAM4 antibody or fragments thereof are replaced by their murine counterparts. It is also preferred that a combination of framework sequences from two different human antibodies is used for VH. The constant domains of the antibody molecule are derived from those of a human antibody.

RS7 Antibody

The RS7 antibody is a murine IgG$_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue. (Stein et al., 1990) EGP-1 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Id.) Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for immunotoxin production. (Id.) It is well documented that internalization of immunotoxin conjugates is a requirement for anti-tumor activity. (Pastan et al., Cell 47:641, 1986) Internalization of drug immunoconjugates has been described as a major factor in anti-tumor efficacy. (Yang et al., Proc. Nat'l Acad. Sci. USA 85: 1189, 1988) Thus, the RS7 antibody exhibits several important properties for therapeutic applications.

Antibody Preparation

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and IgG$_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies and Target Antigens

As discussed above, in preferred embodiments the immunoconjugate antibodies are of use for treatment of pancreatic cancer. However, the skilled artisan will realize that the invention is not so limited and may be applied to other types of cancer or even other disease states. Non-limiting examples include malignant disease, cardiovascular disease, infectious disease, inflammatory disease, autoimmune disease, immune dysfunction disease (e.g., graft versus host disease or organ transplant rejection) or neurological disease. Exemplary target antigens of use for treating such diseases may include carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

In certain embodiments, such as treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Reports on tumor associated antigens (TAAs) include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361, 644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). TACI and B cell maturation antigen (BCMA) are bound by the tumor necrosis factor homolog—a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, PlGF, ED-B fibronectin, an oncogene, an oncogene product, CD66a-d, necrosis antigens, IL-2, T101, TAG, IL-6, MIF, TRAIL-R1 (DR4) and TRAIL-R2 (DR5).

The skilled artisan will realize that any antibody or fragment known in the art that has binding specificity for a target antigen associated with a disease state or condition may be utilized. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662,378, U.S. patent application Ser. No. 12/846,062, filed Jul. 29, 2010), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.)

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments are antigen binding portions of an antibody, such as F(ab')$_2$, Fab', F(ab)$_2$, Fab, Fv, sFv, scFv and the like. Antibody fragments which recognize specific epitopes can be generated by known techniques. F(ab')$_2$ fragments, for example, can be produced by pepsin digestion of the antibody molecule. These and other methods are described, for example, by Goldenberg, U.S. Pat. Nos. 4,036, 945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.- 2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

An antibody fragment can also be prepared by proteolytic hydrolysis of a full-length antibody or by expression in $E. coli$ or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 kD fragment denoted F(ab')$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

General Techniques for Antibody Cloning and Production

Various techniques, such as production of chimeric or humanized antibodies, may involve procedures of antibody cloning and construction. The antigen-binding Vκ (variable light chain) and V$_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned V$_L$ and V$_H$ genes can be expressed in cell culture as a chimeric Ab as described by Orlandi et al., (*Proc. Natl. Acad. Sci.*, USA, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., *Molecular Cloning*, A laboratory manual, 2$^{nd}$ Ed (1989)). The Vκ sequence for the MAb may be amplified using the primers VK1BACK and VK1FOR (Orlandi et al., 1989) or the extended primer set described by Leung et al. (*BioTechniques*, 15: 286 (1993)). The V$_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for V$_H$ can be subcloned into a similar staging vector, such as the pBluescript-based VHpBS. Expression cassettes containing the Vκ and V$_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the Vκ and V$_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

As discussed in the Examples below, in preferred embodiments the radiolabeled antibody and the drug-conjugated antibody are administered as separate antibodies, either sequentially or concurrently. However, in alternative embodiments the two immunoconjugates may be administered as a single bispecific or multispecific antibody. Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate V$_H$ and V$_L$ domains can be joined with a peptide linker of appropriate composition and length (usually consisting of more than 12 amino acid residues) to form a single-chain Fv (scFv), as discussed above. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL), discussed in more detail below, has been utilized to produce combinations of virtually any desired antibodies, antibody fragments and other effector molecules. Any of the techniques known in the art for making bispecific or multispecific antibodies may be utilized in the practice of the presently claimed methods.

Dock-and-Lock (DNL)

Bispecific or multispecific antibodies or other constructs may be produced using the dock-and-lock technology (see, e.g., U.S. Pat. Nos. 7,550,143; 7,521,056; 7,534,866; 7,527,787 and 7,666,400, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Can et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

In preferred embodiments, the radionuclide and drug are directly attached to the antibodies of interest and administered as immunoconjugates. However, in alternative embodiments the radionuclide and/or drug may be conjugated to a targetable construct that comprises one or more haptens. The hapten is recognized by at least one arm of a bispecific or multispecific antibody that also binds to a tumor-associated antigen or other disease-associated antigen. In this case, the radionuclide and/or drug bind indirectly to the antibodies, via the binding of the targetable construct. This process is referred to as pretargeting.

Pre-targeting is a multistep process originally developed to resolve the slow blood clearance of directly targeting antibodies, which contributes to undesirable toxicity to normal tissues such as bone marrow. With pre-targeting, a radionuclide or other diagnostic or therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074,405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

In preferred embodiments, the radionuclide and drug are attached directly to an antibody or antibody fragment to form an immunoconjugate. Immunoconjugates comprising radionuclides may be formed by direct covalent attachment of the radionuclide to a functional group on the antibody, as in the well known radioiodination of tyrosine residues. Alternatively, the radionuclide may be conjugated to a chelating moiety that is attached to the antibody or fragment thereof. Methods for covalent conjugation of chelating moieties, drugs and other therapeutic agents to antibodies and other proteins are known in the art and any such known method may be utilized.

Therapeutic agents may be attached, for example to reduced SH groups and/or to carbohydrate side chains. A therapeutic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

Methods of conjugation and use of chelating agents to attach radionuclides to proteins are well known in the art (see, e.g., U.S. Pat. No. 7,563,433, the Examples section of which is incorporated herein by reference). Exemplary chelators include but are not limited to DTPA (such as Mx-DTPA), DOTA, TETA, NETA or NOTA. Chelates may be directly linked to antibodies or peptides, for example as disclosed in U.S. Pat. No. 4,824,659, incorporated herein in its entirety by reference. Particularly useful chelating moieties include 2-benzyl-DTPA and its monomethyl and cyclohexyl analogs. Other ring-type chelates such as macrocyclic polyethers are of interest for stably binding radionuclides.

In certain embodiments, radionuclides may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

An alternative method for attaching chelating moieties, drugs or other functional groups to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2]azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted akyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach chelating moieties or drugs to antibodies in vitro.

Methods of Therapeutic Treatment

Various embodiments concern methods of treating a cancer in a subject, comprising administering a therapeutically effective amount of an antibody, fragment or immunoconjugate. In preferred embodiments, the subject is administered a radionuclide-conjugated antibody or fragment and a drug-conjugated antibody or fragment.

The immunoconjugates can be supplemented with the administration, either concurrently or sequentially, of at least one other therapeutic agent. Multimodal therapies may include therapy with other antibodies, such as anti-CD22, anti-CD19, anti-CD20, anti-CD21, anti-CD74, anti-CD80, anti-CD23, anti-CD45, anti-CD46, anti-MIF, anti-EGP-1, anti-CEACAM5, anti-CEACAM6, anti-pancreatic cancer mucin, anti-IGF-1R or anti-HLA-DR (including the invariant chain) antibodies in the form of naked antibodies, fusion proteins, or as immunoconjugates. Various antibodies of use, such as anti-CD19, anti-CD20, and anti-CD22 antibodies, are known to those of skill in the art. See, for example, Ghetie et al., Cancer Res. 48:2610 (1988); Hekman et al., Cancer Immunol. Immunother. 32:364 (1991); Longo, Curr. Opin. Oncol. 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498; the Examples section of each of which is incorporated herein by reference.

In one non-limiting embodiment, the present invention contemplates treatment with conjugated PAM4 and RS7 antibodies or fragments thereof before, in combination with, or after other pancreatic tumor associated antibodies such as CA19.9, DUPAN2, SPAN1, Nd2, B72.3, CC49, anti-Le$^a$ antibodies, and antibodies to other Lewis antigens (e.g., Le(y)), as well as antibodies against carcinoembryonic antigen (CEA or CEACAM5), CEACAM6, colon-specific antigen-p (CSAp), MUC-1, MUC-2, MUC-3, MUC-4, MUC-5ac, MUC-16, MUC-17, HLA-DR, CD40, CD74, CD138, HER2/neu, EGFR, EGP-1, EGP-2, angiogenesis factors (e.g., VEGF, PlGF), insulin-like growth factor (ILGF), tenascin, platelet-derived growth factor, and IL-6, as well as products of oncogenes (e.g., bcl-2, Kras, p53), cMET, and antibodies against tumor necrosis substances. These solid tumor antibodies may be naked or conjugated to, inter alia, drugs, toxins, isotopes, radionuclides or immunomodulators. Many different antibody combinations may be constructed and used in either naked or conjugated form. Alternatively, different antibody combinations may be employed for administration in combination with other therapeutic agents, such as a cytotoxic drug or with radiation, given consecutively, simultaneously, or sequentially.

In another form of multimodal therapy, subjects receive immunoconjugates in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

In a preferred multimodal therapy, both chemotherapeutic drugs and cytokines are co-administered with an antibody or immunoconjugate. The cytokines, chemotherapeutic drugs and antibody or immunoconjugate can be administered in any order, or together.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate of the present invention can be formulated for intravenous administration via, for example, bolus injection or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate or antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate may also be administered to a mammal subcutaneously or even by other parenteral routes. Moreover, the administration may be by continuous infusion or by single or multiple boluses. Preferably, the antibody is infused over a period of less than about 4 hours, and more preferably, over a period of less than about 3 hours.

More generally, the dosage of an administered immunoconjugate for humans will vary depending upon such factors as the patient's age, weight, height, sex, general medical condition and previous medical history. It may be desirable to provide the recipient with a dosage of immunoconjugate, antibody fusion protein that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an antibody may be administered as one dosage every 2 or 3 weeks, repeated for a total of at least 3 dosages. Or, the antibodies may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the subject antibodies are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Other Therapeutic Agents

A wide variety of therapeutic reagents can be administered concurrently or sequentially, or advantageously conjugated to the antibodies of the invention, for example, drugs, toxins, oligonucleotides, immunomodulators, hormones, hormone antagonists, enzymes, enzyme inhibitors, radionuclides, angiogenesis inhibitors, etc. The therapeutic agents recited here are those agents that also are useful for administration separately with an antibody as described above. Therapeutic agents include, for example, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, taxol, CPT-11, camptothecans, proteosome inhibitors, mTOR inhibitors, HDAC inhibitors, tyrosine kinase inhibitors, and others. Other useful cancer chemotherapeutic drugs for administering concurrently or sequentially, or for the preparation of immunoconjugates and antibody fusion proteins include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

In a preferred embodiment, conjugates of camptothecins and related compounds, such as SN-38, may be conjugated to hPAM4, hRS7 or other anti-pancreatic cancer antibodies, for example as disclosed in U.S. patent application Ser. No. 12/026,811, filed Feb. 6, 2008; and Ser. No. 11/388,032, filed Mar. 23, 2006, the Examples section of each of which is incorporated herein by reference. In another preferred embodiment, gemcitabine is administered to the subject in conjunction with $^{90}$Y-hPAM4 and/or SN-38-hRS7.

A toxin can be of animal, plant or microbial origin. A toxin, such as *Pseudomonas* exotoxin, may also be complexed to or form the therapeutic agent portion of an immunoconjugate of the antibodies. Other toxins suitably employed in the preparation of such conjugates or other fusion proteins, include ricin, abrin, ribonuclease (RNase), DNase I, Staphylococcal enterotoxin-A, pokeweed antiviral protein, onconase, gelonin, diphtheria toxin, *Pseudomonas* exotoxin, and *Pseudomonas* endotoxin. See, for example, Pastan et al., Cell 47:641 (1986), Goldenberg, C A—A Cancer Journal for Clinicians 44:43 (1994), Sharkey and Goldenberg, C A—A Cancer Journal for Clinicians 56:226 (2006). Additional toxins suitable for use are known to those of skill in the art and are disclosed in U.S. Pat. No. 6,077,499, the Examples section of which is incorporated herein by reference.

An immunomodulator, such as a cytokine, may also be conjugated to, or form the therapeutic agent portion of the immunoconjugate, or may be administered with, but unconjugated to, an antibody or antibody fragment. As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (ILGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin and LT, and the like.

The immunoconjugate may comprise one or more radioactive isotopes useful for treating diseased tissue. Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5-hour half-life and abundant supply of beta particles and gamma rays, can be conjugated to an antibody using the chelating agent, p-bromoacetamido-benzyl-tetraethylaminetetraacetic acid (TETA). Chase, supra. Alternatively, $^{90}$Y, which emits an energetic beta particle, can be coupled to an antibody, antibody fragment or fusion protein, using diethylenetriaminepentaacetic acid (DTPA), or more preferably using DOTA. Methods of conjugating $^{90}$Y to antibodies or targetable constructs are known in the art and any such known methods may be used. (See, e.g., U.S. Pat. No. 7,259,249, the Examples section of which is incorporated herein by reference. See also Linden et al., Clin Cancer Res. 11:5215-22, 2005; Sharkey et al., J Nucl Med. 46:620-33, 2005; Sharkey et al., J Nucl Med. 44:2000-18, 2003.)

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used in combination with a naked or conjugated antibody or antibody fragment. For example, the radiosensitizer can be used in combination with a radiolabeled antibody or antibody fragment. The addition of the radiosensitizer can result in enhanced efficacy when compared to treatment with the radiolabeled antibody or antibody fragment alone. Radiosensitizers are described in D. M. Goldenberg (ed.), CANCER THERAPY WITH RADIOLABELED ANTIBODIES, CRC Press (1995). Other typical radionsensitizers of interest for use with this technology include gemcitabine, 5-fluorouracil, and cisplatin, and have been used in combination with external irradiation in the therapy of diverse cancers, including pancreatic cancer. Therefore, we have studied the combination of gemcitabine at what is believed to be radiosensitizing doses (once weekly 200 m g/m$^2$ over 4 weeks) of gemcitabine combined with fractionated doses of $^{90}$Y-hPAM4, and have observed objective evidence of pancreatic cancer reduction after a single cycle of this combination that proved to be well-tolerated (no grade 3-4 toxicities by NCI-CTC v. 3 standard).

Antibodies or fragments thereof that have a boron addend-loaded carrier for thermal neutron activation therapy will normally be affected in similar ways. However, it will be advantageous to wait until non-targeted immunoconjugate clears before neutron irradiation is performed. Clearance can be accelerated using an anti-idiotypic antibody that binds to the anti-pancreatic cancer antibody. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the antibody conjugate, a boron addend is activated by thermal neutron irradiation and converted to radioactive atoms which decay by alpha-emission to produce highly toxic, short-range effects.

Pharmaceutically Suitable Excipients

The antibodies, fragments thereof or immunoconjugates to be delivered to a subject can comprise one or more pharmaceutically suitable excipients, one or more additional ingredients, or some combination of these. The antibody can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Kits

Various embodiments may concern kits containing components suitable for treating or diagnosing diseased tissue in a patient. Exemplary kits may contain at least one antibody, antigen binding fragment or fusion protein as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, an anti-pancreatic cancer antibody or antigen binding fragment thereof may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions for use of the kit.

EXAMPLES

The examples below are illustrative of embodiments of the current invention and are not limiting to the scope of the claims.

Example 1

Therapy of a Patient with Inoperable and Metastatic Pancreatic Carcinoma

Figure 2:
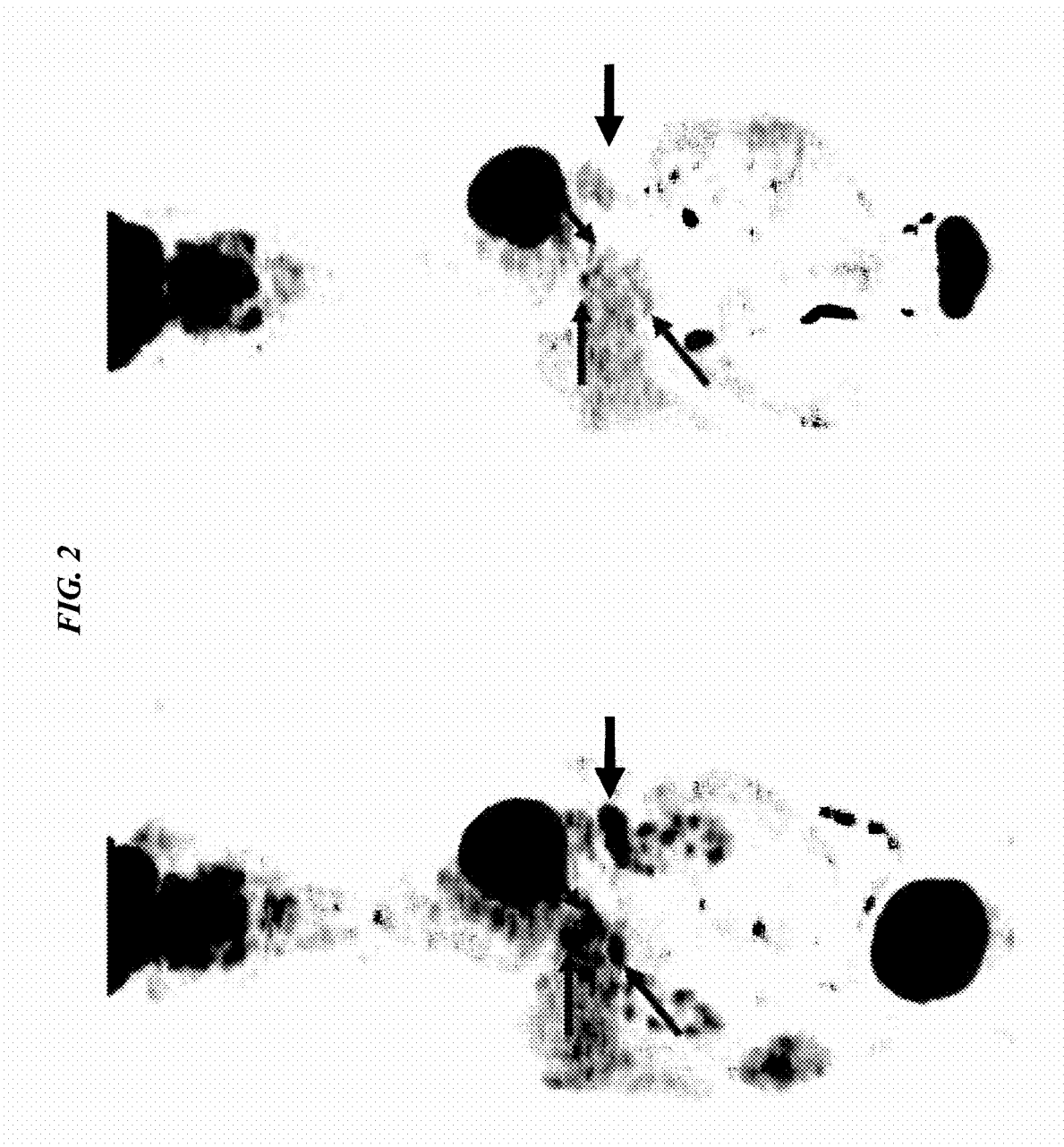
FIG. 2. 3D PET images for a patient with inoperable metastatic pancreatic cancer treated with fractionated $^{90}$Y-hPAM4 plus gemcitabine, before therapy (left side) and post-therapy (right side). Arrows point to the locations of the primary lesion (on right) and metastases (on left), each of which shows a significant decrease in PET image intensity after therapy with radiolabeled hPAM4 plus gemcitabine.

The humanized PAM4 (hPAM4) antibody was made and radiolabeled as described in U.S. Pat. No. 7,282,567 (incorporated herein by reference in its entirety). Patient 118-001, CWG, was a 63-year-old man with Stage-IV pancreatic adenocarcinoma with multiple liver metastases, diagnosed in November of 2007. He agreed to undertake combined radioimmunotherapy and gemcitabine chemotherapy as a first treatment strategy, and was then given a first therapy cycle of 6.5 mCi/m$^2$ of $^{90}$Y-hPAM4, combined with 200 mg/m$^2$ gemcitabine, whereby the gemcitabine was given once weekly on weeks 1-4 and $^{90}$Y-hPAM4 was given once-weekly on weeks 2-4 (3 doses). Two months later, the same therapy cycle was repeated, because no major toxicities were noted after the first cycle. Already 4 weeks after the first therapy cycle, CT evidence of a reduction in the diameters of the primary tumor and 2 of the 3 liver metastases surprisingly was noted, and this was consistent with significant decreases in the SUV values of FDG-PET scans, with 3 of the 4 tumors returning to normal background SUV levels at this time (FIG. 1 and FIG. 2). The patient's pre-therapy CA-19.9 level of 1,297 dropped to a low level of 77, further supportive of the therapy being effective.

Table 1 shows the effects of combined radioimmunotherapy with $^{90}$Y-hPAM4 and gemcitabine chemotherapy in this patient. It was surprising and unexpected that such low doses of the radionuclide conjugated to the antibody combined with such low, nontoxic, doses of gemcitabine showed such anti-tumor activity even after only a single course of this therapy.

TABLE 1

Effects of Combined Radioimmunotherapy with $^{90}$Y-hPAM4 and Gemcitabine Chemotherapy in Metastatic Pancreatic Carcinoma

| Tumor Location | Baseline Longest Diameter (cm) | 4 wk post-Tx Longest Diameter (cm) | Baseline PET (SUV) | 4 wk post-Tx PET (SUV) |
|---|---|---|---|---|
| Pancreatic tail (primary) | 4.5 | 4.3 | 9.2 | 4.2 |
| L hepatic met | 1.9 | 1.9 | 4.1 | background |
| R post hepatic met | 1.7 | 1.6 | 3.7 | background |
| R central hepatic met | 1.9 | 1.2 | 3.2 | background |

Example 2

Therapy of Pancreatic Cancer Xenografts with Gemcitabine and $^{90}$Y-Labeled Peptide Pretargeted Using TF10

Summary $^{90}$Y-hPAM4 IgG is currently being examined in Phase I/II trials in combination with gemcitabine in patients with Stage III/IV pancreatic cancer. We disclose a new approach for pretargeting radionuclides that is able to deliver a similar amount of radioactivity to pancreatic cancer xenografts, but with less hematological toxicity, which would be more amenable for combination with gemcitabine. The TF10 bispecific antibody was made by the DNL technique as described below. Nude mice bearing ~0.4 cm$^3$ sc CaPan1 human pancreatic cancer were administered TF10, followed 1 day later with a $^{90}$Y-labeled hapten-peptide (IMP-288). Various doses and schedules of gemcitabine were added to this treatment, and tumor progression monitored up to 28 weeks. 0.7 mCi PT-RAIT alone produced only a transient 60% loss in blood counts, and animals given 0.9 mCi of PT-RAIT alone and 0.7 mCi PT-RAIT+6 mg gemcitabine (human equivalent ~1000 mg/m$^2$) had no histological evidence of renal toxicity after 9 months. A single dose of 0.25 or 0.5 mCi PT-RAIT alone can completely ablate 20% and 80% of the tumors, respectively. Monthly fractionated PT-RAIT (0.25 mCi/dose given at the start of each gemcitabine cycle) added to a standard gemcitabine regimen (6 mg wkly×3; 1 wk off; repeat 3 times) significantly increased the median time for tumors to reach 3.0 cm$^3$ over PT-RAIT alone. Other treatment plans examining non-cytotoxic radiosensitizing dose regimens of gemcitabine added to PT-RAIT also showed significant improvements in treatment response over PT-RAIT alone. The results show that PT-RAIT is a promising new approach for treating pancreatic cancer. These data indicate combining PT-RAIT with gemcitabine will enhance therapeutic responses.

Methods

TF10 bispecific antibody was prepared as described below. For pretargeting, TF10 was given to nude mice bearing the human pancreatic adenocarcinoma cell line, CaPan1. After allowing sufficient time for TF10 to clear from the blood (16 h), the radiolabeled divalent HSG-peptide was administered. The small molecular weight HSG-peptide (~1.4 kD) clears within minutes from the blood, entering the extravascular space where it can bind to anti-HSG arm of the pretargeted TF10 bsMAb. Within a few hours, >80% of the radiolabeled HSG-peptide is excreted in the urine, leaving the tumor localized peptide and a trace amount in the normal tissues.

Results

Figure 3:
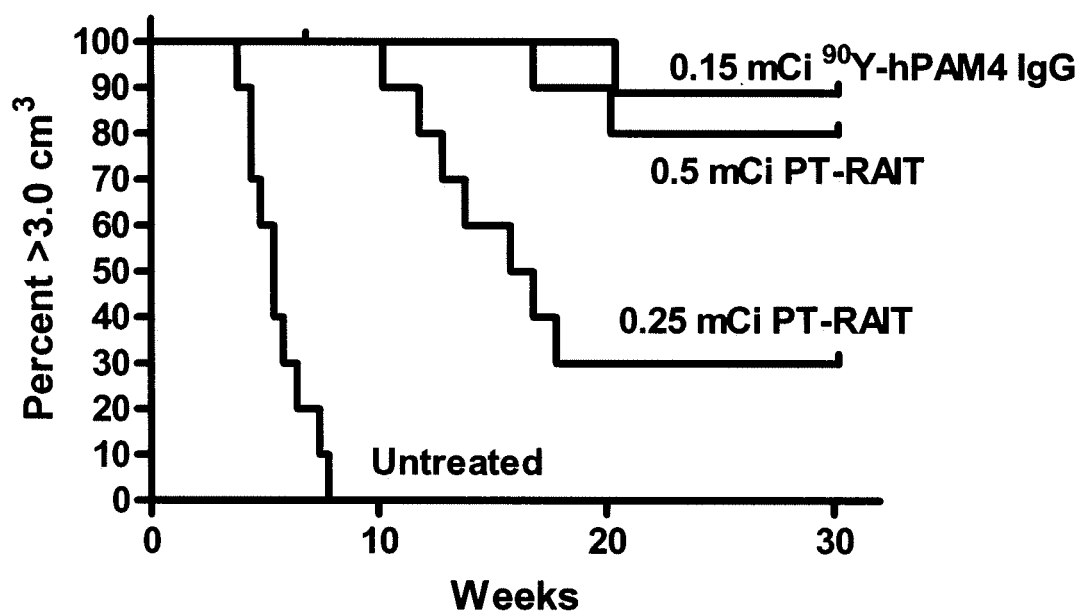
FIG. 3. Therapeutic activity of a single treatment of established (~0.4 cm$^3$) CaPan1 tumors with 0.15 mCi of $^{90}$Y-hPAM4 IgG, or 0.25 or 0.50 mCi of TF10-pretargeted $^{90}$Y-IMP-288.

FIG. 3 illustrates the therapeutic activity derived from a single treatment of established (~0.4 cm$^3$) CaPan1 tumors with 0.15 mCi of $^{90}$Y-hPAM4 IgG, or 0.25 or 0.50 mCi of TF10-pretargeted $^{90}$Y-IMP-288. Similar anti-tumor activity was observed for the 0.5-mCi pretargeted dose vs. 0.15-mCi dose of the directly radiolabeled IgG, but hematological toxicity was severe at this level of the direct conjugate (not shown), while the pretargeted dose was only moderately toxic (not shown). Indeed, the MTD for pretargeting using 90Y-IMP-288 is at least 0.9 mCi in nude mice.

Figure 4:
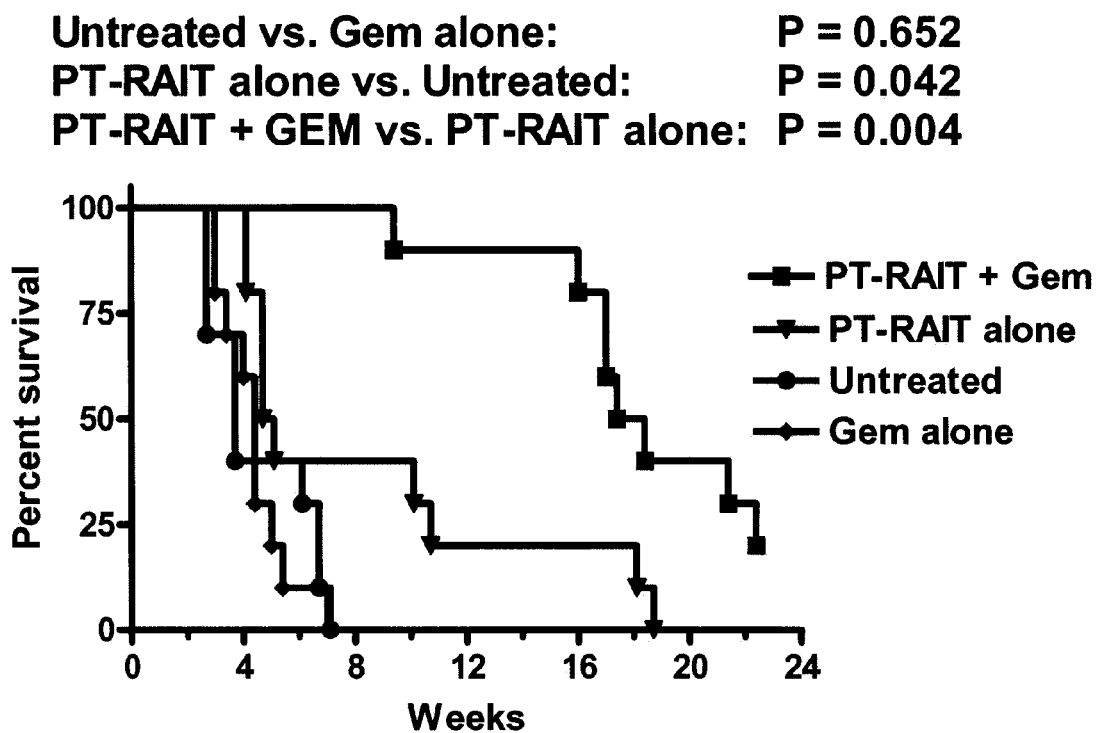
FIG. 4. Effect of gemcitabine potentiation of PT-RAIT therapy.

FIG. 4 shows that the combination of gemcitabine and PT-RAIT has a synergistic effect on anti-tumor therapy. Human equivalent doses of 1000 mg/m$^2$ (6 mg) of gemcitabine (GEM) were given intraperitoneally to mice weekly for 3 weeks, then after resting for 1 week, this regimen was repeated 2 twice. PT-RAIT (0.25 mCi of TF10-pretargeted $^{90}$Y-IMP-288) was given 1 day after the first GEM dose in each of the 3 cycles of treatment. GEM alone had no significant impact on tumor progression (survival based on time to progress to 3.0 cm$^3$). PT-RAIT alone improved survival compared to untreated animals, but the combined GEM with PT-RAIT regimen increased the median survival by nearly 10 weeks. Because hematological toxicity is not dose-limiting for PT-RAIT, but it is one of the limitations for gemcitabine therapy, these studies suggest that PT-RAIT could be added to a standard GEM therapy with the potential for enhanced responses. The significant synergistic effect of gemcitabine plus PT-RAIT was surprising and unexpected.

A further study examined the effect of the timing of administration on the potentiation of anti-tumor effect of gemcitabine plus PT-RAIT. A single 6-mg dose of GEM was given one day before or 1 day after 0.25 mCi of TF10-pretargeted $^{90}$Y-IMP-288 (not shown). This study confirmed what is already well known with GEM, i.e., radiosensitization is best given in advance of the radiation. Percent survival of treated mice showed little difference in survival time between PT-RAIT alone and PT-RAIT with gemcitabine given 22 hours after the radiolabeled peptide. However, administration of gemcitabine 19 hours prior to PT-RAIT resulted in a substantial increase in survival (not shown).

Figure 5:
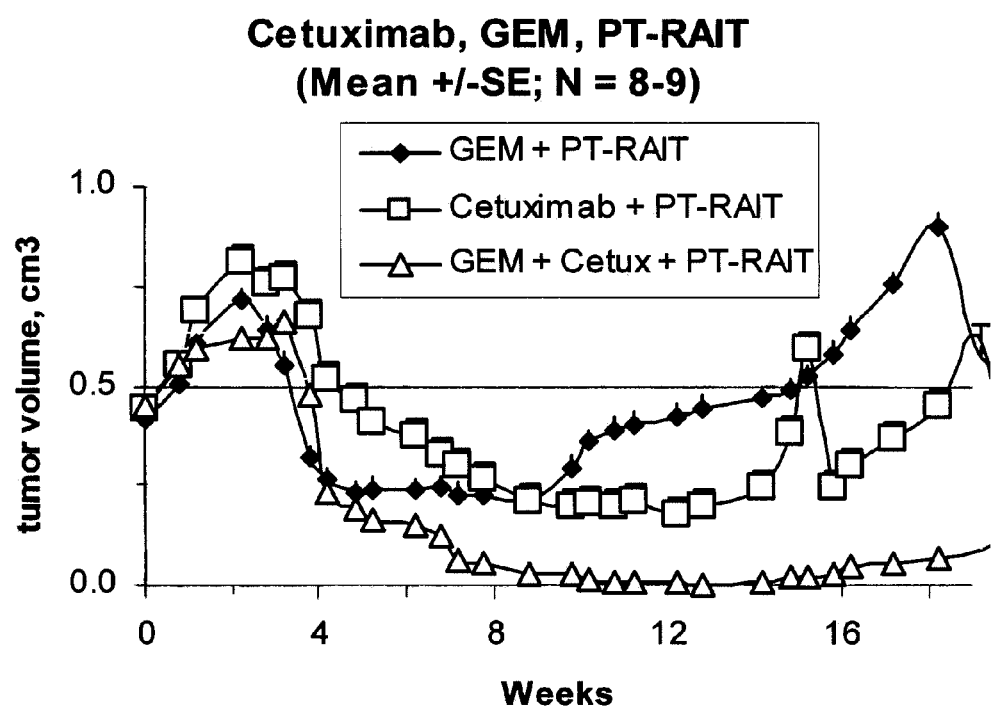
FIG. 5. Effect of combination of cetuximab with gemcitabine and PT-RAIT.

Single dose PT-RAIT (0.25 mCi) combined with cetuximab (1 mg weekly ip; 7 weeks) or with cetuximab+GEM (6 mg weekly×3) in animals bearing CaPan1 showed the GEM+cetuximab combination with PT-RAIT providing a better initial response (FIG. 5), but the response associated with just cetuximab alone added to PT-RAIT was encouraging (FIG. 5), since it was as good or better than PT-RAIT+GEM. Because the overall survival in this study was excellent, with only 2 tumors in each group progressing to >2.0 cm3 after 24 weeks when the study was terminated, these results indicate a potential role for cetuximab when added to PT-RAIT.

Example 3

Effect of Fractionated Pretargeted Radioimmunotherapy (PT-RAIT) for Pancreatic Cancer Therapy We evaluated fractionated therapy with $^{90}$Y-DOTA-di-HSG peptide (IMP-288) and TF10. Studies using TF10 and radiolabeled IMP-288 were performed in nude mice bearing s.c. CaPan1 human pancreatic cancer xenografts, 0.32-0.54 cm$^3$. For therapy, TF10-pretargeted $^{90}$Y-IMP-288 was given

[A] once (0.6 mCi on wk 0) or [B] fractionated (0.3 mCi on wks 0 and 1), [C] (0.2 mCi on wks 0, 1 and 2) or [D] (0.2 mCi on wks 0, 1 and 4).

Tumor regression (>90%) was observed in the majority of mice, 9/10, 10/10, 9/10 and 8/10 in groups [A], [B], [C] and [D], respectively. In group [A], maximum tumor regression in 50% of the mice was reached at 3.7 wks, compared to 6.1, 8.1 and 7.1 wks in [B], [C] and [D], respectively. Some tumors showed regrowth. At week 14, the best therapeutic response was observed in the fractionated group (2×0.3 mCi), with 6/10 mice having no tumors (NT) compared to 3/10 in the 3×0.2 mCi groups and 1/10 in the 1×0.6 mCi group. No major body weight loss was observed. Fractionated PT-RAIT provides another alternative for treating pancreatic cancer with minimum toxicity.

Example 4

$^{90}$Y-hPAM4 Radioimmunotherapy (RAIT) Plus Radiosensitizing Gemcitabine (GEM) Treatment in Advanced Pancreatic Cancer (PC)

$^{90}$Y-hPAM4, a humanized antibody highly specific for PC, showed transient activity in patients with advanced disease, and GEM enhanced RAIT in preclinical studies. This study evaluated repeated treatment cycles of $^{90}$Y-hPAM4 plus GEM in patients with untreated, unresectable PC. The $^{90}$Y-dose was escalated by cohort, with patients repeating 4-wk cycles (once weekly 200 mg/m$^2$ GEM, $^{90}$Y-hPAM4 once-weekly wks 2-4) until progression or unacceptable toxicity. Response assessments used CT, FDG-PET, and CA19.9 serum levels.

Of 8 patients (3F/5M, 56-72 y.o.) at the 1$^{st}$ 2 dose levels (6.5 and 9.0 mCi/m$^2$ $^{90}$Y-hPAM4×3), hematologic toxicity has been transient Grade 1-2. Two patients responded to initial treatment with FDG SUV and CA19.9 decreases, and lesion regression by CT. Both patients continue in good performance status now after 9 and 11 mo. and after a total of 3 and 4 cycles, respectively, without additional toxicity. A 3$^{rd}$ patient with a stable response by PET and CT and decreases in CA19.9 levels after initial treatment is now undergoing a 2nd cycle. Four other patients had early disease progression and the remaining patient is still being evaluated. Dose escalation is continuing after fractionated RAIT with $^{90}$Y-hPAM4 plus low-dose gemcitabine demonstrated therapeutic activity at the initial $^{90}$Y-dose levels, with minimal hematologic toxicity, even after 4 therapy cycles.

Example 5

PAM4 Antibody Binds to the Earliest Stages of Pancreatic Cancer

Immunohistochemistry studies were performed with PAM4 antibody. Results obtained with stained tissue sections showed no reaction of PAM4 with normal pancreatic ducts, ductules and acinar tissues (not shown). In contrast, use of the MA5 antibody applied to the same tissue samples showed diffuse positive staining of normal pancreatic ducts and acinar tissue (not shown). In tissue sections with well differentiated or moderately differentiated pancreatic adenocarcinoma, PAM4 staining was positive, with mostly cytoplasmic staining but intensification of at the cell surface. Normal pancreatic tissue in the same tissue sections was unstained.

Table 2 shows the results of immunohistochemical analysis with PAM4 MAb in pancreatic adenocarcinoma samples of various stages of differentiation. Overall, there was an 87% detection rate for all pancreatic cancer samples, with 100% detection of well differentiated and almost 90% detection of moderately differentiated pancreatic cancers.

TABLE 2

PAM4 Binding to Different Stages of Pancreatic Cancer

| Cancer | n | Focal | Diffuse | Total |
|---|---|---|---|---|
| Well Diff. | 13 | 2 | 11 | 13 (100%) |
| Moderately Diff. | 24 | 6 | 15 | 21 (88%) |
| Poorly Diff. | 18 | 5 | 9 | 14 (78%) |
| Total | 55 | 13 | 35 | 48 (87%) |

Table 3 shows that PAM4 immunohistochemical staining also detected a very high percentage of precursor lesions of pancreatic cancer, including PanIn-1A to PanIN-3, IPMN (intraductal papillary mucinous neoplasms) and MCN (mucinous cystic neoplasms). Overall, PAM4 staining detected 89% of all pancreatic precursor lesions. These results demonstrate that PAM4 antibody-based immunodetection is capable of detecting almost 90% of pancreatic cancers and precursor lesions by in vitro analysis. PAM4 expression was observed in the earliest phases of PanIN development. Intense staining was observed in IPMN and MCN samples (not shown). The PAM4 epitope was present at high concentrations (intense diffuse stain) in the great majority of pancreatic adenocarcinomas. PAM4 showed diffuse, intense reactivity with the earliest stages of pancreatic carcinoma precursor lesions, including PanIN-1, IPMN and MCN, yet was non-reactive with normal pancreatic tissue. Taken together, these results show that the PAM4 antibody is binds with very high specificity to the earliest stages of pancreatic cancer development.

TABLE 3

PAM4 Banding to Precursor Lesions of Pancreatic Cancer

| | n | Focal | Diffuse | Total |
|---|---|---|---|---|
| PanIn-1A | 27 | 9 | 15 | 24 (89%) |
| PanIn-1B | 20 | 4 | 16 | 20 (100%) |
| PanIn-2 | 11 | 6 | 4 | 10 (91%) |
| PanIn-3 | 5 | 2 | 0 | 2 (40%) |
| Total PanIn | 63 | 21 | 35 | 56 (89%) |
| IPMN | 36 | 6 | 25 | 31 (86%) |
| MCN | 27 | 3 | 22 | 25 (92%) |

Example 6

Preparation of Dock-and-Lock (DNL) Constructs

DDD and AD Fusion Proteins

The DNL technique can be used to make dimers, trimers, tetramers, hexamers, etc. comprising virtually any antibodies or fragments thereof or other effector moieties. For certain preferred embodiments, IgG antibodies or Fab antibody fragments may be produced as fusion proteins containing either a dimerization and docking domain (DDD) or anchoring domain (AD) sequence. Although in preferred embodiments the DDD and AD moieties are produced as fusion proteins, the skilled artisan will realize that other methods of conjugation, such as chemical cross-linking, may be utilized within the scope of the claimed methods and compositions.

Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. The technique is not limiting and any protein or peptide of use may be produced as an AD or DDD fusion protein for incorporation into a DNL construct. Where chemical cross-linking is utilized, the AD and DDD conjugates are not limited to proteins or peptides and may comprise any molecule that may be cross-linked to an AD or DDD sequence using any cross-linking technique known in the art. In certain exemplary embodiments, a polyethylene glycol (PEG) or other polymeric moiety may be incorporated into a DNL construct, as described in further detail below.

For pretargeting applications, an antibody or fragment containing a binding site for an antigen associated with a diseased tissue, such as a tumor-associated antigen (TAA), may be combined with a second antibody or fragment that binds a hapten on a targetable construct, to which a therapeutic and/or diagnostic agent is attached. The DNL-based bispecific antibody is administered to a subject, circulating antibody is allowed to clear from the blood and localize to target tissue, and the conjugated targetable construct is added and binds to the localized antibody for diagnosis or therapy.

Independent transgenic cell lines may be developed for each Fab or IgG fusion protein. Once produced, the modules can be purified if desired or maintained in the cell culture supernatant fluid. Following production, any DDD-fusion protein module can be combined with any AD-fusion protein module to generate a bispecific DNL construct. For different types of constructs, different AD or DDD sequences may be utilized. Exemplary DDD and AD sequences are provided below.

```
DDD1:
                                              (SEQ ID NO: 13)
SHIQIPPGLTELLQGYTVEVLRQQPPDLVEFAVEYFTRLREARA

DDD2:
                                              (SEQ ID NO: 14)
CGHIQIPPGLTELLQGYTVEVLRQQPPDLVEFAVEYFTRLREARA

AD1:
                                              (SEQ ID NO: 15)
QIEYLAKQIVDNAIQQA

AD2:
                                              (SEQ ID NO: 16)
CGQIEYLAKQIVDNAIQQAGC
```

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                              (SEQ ID NO: 17)
SLRECELYVQKHNIQALLKDSIVQLCTARPERPMAFLREYFERLEKEEAK

DDD3C
                                              (SEQ ID NO: 18)
MSCGGSLRECELYVQKHNIQALLKDSIVQLCTARPERPMAFLREYFERLE
KEEAK

AD3
                                              (SEQ ID NO: 19)
CGFEELAWKIAKMIWSDVFQQGC
```

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIa dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3'end. The encoded polypeptide sequence is shown below.

```
                                              (SEQ ID NO: 20)
GSGGGGSGGGGSHIQIPPGLTELLQGYTVEVLRQQPPDLVEFAVEYFTR
LREARA
```

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3'end. The encoded polypeptide sequence is shown below.

(SEQ ID NO: 21)
GSGGGGSGGGGSQIEYLAKQIVDNAIQQA

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchoring domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of a₂b formation. Addition of 5 mM TCEP rapidly resulted in the formation of a₂b complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of a₄, a₂ and free kappa chains from the product (not shown).

The functionality of TF2 was determined by BIACORE® assay. TF2, C-DDD1-hMN-14+h679-AD1 (used as a control sample of noncovalent a₂b complex), or C-DDD2-hMN-14+h679-AD2 (used as a control sample of unreduced a₂ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Production of TF10 Bispecific Antibody

A similar protocol was used to generate a trimeric TF10 DNL construct, comprising two copies of a C-DDD2-Fab-hPAM4 and one copy of C-AD2-Fab-679. The cancer-targeting antibody component in TF10 was derived from hPAM4, a humanized anti-pancreatic cancer mucin MAb that has been studied in detail as a radiolabeled MAb (e.g., Gold et al., Clin. Cancer Res. 13: 7380-7387, 2007). The hapten-binding component was derived from h679, a humanized anti-histaminyl-succinyl-glycine (HSG) MAb. The TF10 bispecific ([hPAM4]₂×h679) antibody was produced using the method disclosed for production of the (anti CEA)₂×anti HSG bsAb TF2, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

A full tissue histology and blood cell binding panel has been examined for hPAM4 IgG and for an anti-CEA×anti-HSG bsMAb that is entering clinical trials. hPAM4 binding was restricted to very weak binding to the urinary bladder and stomach in 1/3 specimens (no binding was seen in vivo), and no binding to normal tissues was attributed to the anti-CEA×anti-HSG bsMAb. Furthermore, in vitro studies against cell lines bearing the H1 and H2 histamine receptors showed no antagonistic or agonistic activity with the IMP 288 di-HSG peptide, and animal studies in 2 different species showed no pharmacologic activity of the peptide related to the histamine component at doses 20,000 times higher than that used for imaging. Thus, the HSG-histamine derivative does not have pharmacologic activity.

The skilled artisan will realize that the DNL techniques disclosed above may be used to produce complexes comprising any combination of antibodies or immunoconjugates—for example, a radiolabeled hPAM4 and an SN-38 conjugated hRS7 DNL complex.

Example 7

Sequence Variants for DNL

In certain preferred embodiments, the AD and DDD sequences incorporated into the DNL complex comprise the amino acid sequences of AD1 or AD2 and DDD1 or DDD2, as discussed above. However, in alternative embodiments sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 22)
SLRECELYVQKHNIQALLKDVSIVQLCTARPERPMAFLREYFEKLEKEE
AK

PKA RIβ
(SEQ ID NO: 23)
SLKGCELYVQLHGIQQVLKDCIVHLCISKPERPMKFLREHFEKLEKEEN
RQILA

PKA RIIα
(SEQ ID NO: 24)
SHIQIPPGLTELLQGYTVEVGQQPPDLVDFAVEYFTRLREARRQ

PKA RIIβ
(SEQ ID NO: 25)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:13 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 13)
SHIQIPPGLTELLQGYTVEVLRQQPPDLVEFAVEYFTRLREARA

Alto et al. (2003) performed a bioinformatic analysis of the AD sequence of various AKAP proteins to design an RII selective AD sequence called AKAP-IS (SEQ ID NO:15), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:15. The skilled artisan will realize that in designing sequence variants of the AD sequence, one would desirably avoid changing any of the underlined residues, while conservative amino acid substitutions might be made for residues that are less critical for DDD binding.

```
AKAP-IS sequence
                                        (SEQ ID NO: 15)
QIEYLAKQIVDNAIQQA
```

Gold (2006) utilized crystallography and peptide screening to develop a SuperAKAP-IS sequence (SEQ ID NO:26), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIa. In this sequence, the N-terminal Q residue is numbered as residue number 4 and the C-terminal A residue is residue number 20. Residues where substitutions could be made to affect the affinity for RIIa were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:27-29. Substitutions relative to the AKAP-IS sequence are underlined. It is anticipated that, as with the AD2 sequence shown in SEQ ID NO:16, the AD moiety may also include the additional N-terminal residues cysteine and glycine and C-terminal residues glycine and cysteine.

```
SuperAKAP-IS
                                        (SEQ ID NO: 26)
QIEYVAKQIVDYAIHQA Alternative AKAP sequences
                                        (SEQ ID NO: 27)
QIEYKAKQIVDHAIHQA (SEQ ID NO: 28)
QIEYHAKQIVDHAIHQA (SEQ ID NO: 29)
QIEYVAKQIVDHAIHQA
```

FIG. 2 of Gold et al. disclosed additional DDD-binding sequences from a variety of AKAP proteins, shown below.

```
RII-Specific AKAPs
AKAP-KL
                                        (SEQ ID NO: 30)
PLEYQAGLLVQNAIQQAI AKAP79
                                        (SEQ ID NO: 31)
LLIETASSLVKNAIQLSI AKAP-Lbc
                                        (SEQ ID NO: 32)
LIEEAASRIVDAVIEQVK RI-Specific AKAPs
AKAPce
                                        (SEQ ID NO: 33)
ALYQFADRFSELVISEAL

RIAD
                                        (SEQ ID NO: 34)
LEQVANQLADQIIKEAT

PV38
                                        (SEQ ID NO: 35)
FEELAWKIAKMIWSDVF

Dual-Specificity AKAPs
AKAP7
                                        (SEQ ID NO: 36)
ELVRLSKRLVENAVLKAV

MAP2D
                                        (SEQ ID NO: 37)
TAEEVSARIVQVVTAEAV

DAKAP1
                                        (SEQ ID NO: 38)
QIKQAAFQLISQVILEAT

DAKAP2
                                        (SEQ ID NO: 39)
LAWKIAKMIVSDVMQQ
```

Stokka et al. (2006) also developed peptide competitors of AKAP binding to PKA, shown in SEQ ID NO:40-42. The peptide antagonists were designated as Ht31 (SEQ ID NO:40), RIAD (SEQ ID NO:41) and PV-38 (SEQ ID NO:42). The Ht-31 peptide exhibited a greater affinity for the RII isoform of PKA, while the RIAD and PV-38 showed higher affinity for RI.

```
Ht31
                                        (SEQ ID NO: 40)
DLIEEAASRIVDAVIEQVKAAGAY

RIAD
                                        (SEQ ID NO: 41)
LEQYANQLADQIIKEATE

PV-38
                                        (SEQ ID NO: 42)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 15) |
| AKAPIS-P | QIEYLAKQIPDNAIQQA (SEQ ID NO: 43) |

TABLE 4-continued

AKAP Peptide sequences

| | Peptide Sequence |
|---|---|
| Ht31 | KGADLIEEAASRIVDAVIEQVKAAG (SEQ ID NO: 44) |
| Ht31-P | KGADLIEEAASRIPDAPIEQVKAAG (SEQ ID NO: 45) |
| AKAP7δ-wt-pep | PEDAELVRLSKRLVENAVLKAVQQY (SEQ ID NO: 46) |
| AKAP7δ-L304T-pep | PEDAELVRTSKRLVENAVLKAVQQY (SEQ ID NO: 47) |
| AKAP7δ-L308D-pep | PEDAELVRLSKRDVENAVLKAVQQY (SEQ ID NO: 48) |
| AKAP7δ-P-pep | PEDAELVRLSKRLPENAVLKAVQQY (SEQ ID NO: 49) |
| AKAP7δ-PP-pep | PEDAELVRLSKRLPENAPLKAVQQY (SEQ ID NO: 50) |
| AKAP7δ-L314E-pep | PEDAELVRLSKRLVENAVEKAVQQY (SEQ ID NO: 51) |
| AKAP1-pep | EEGLDRNEEIKRAAFQIISQVISEA (SEQ ID NO: 52) |
| AKAP2-pep | LVDDPLEYQAGLLVQNAIQQAIAEQ (SEQ ID NO: 53) |
| AKAP5-pep | QYETLLIETASSLVKNAIQLSIEQL (SEQ ID NO: 54) |
| AKAP9-pep | LEKQYQEQLEEEVAKVIVSMSIAFA (SEQ ID NO: 55) |
| AKAP10-pep | NTDEAQEELAWKIAKMIVSDIMQQA (SEQ ID NO: 56) |
| AKAP11-pep | VNLDKKAVLAEKIVAEAIEKAEREL (SEQ ID NO: 57) |
| AKAP12-pep | NGILELETKSSKLVQNIIQTAVDQF (SEQ ID NO: 58) |
| AKAP14-pep | TQDKNYEDELTQVALALVEDVINYA (SEQ ID NO: 59) |
| Rab32-pep | ETSAKDNINIEEAARFLVEKILVNH (SEQ ID NO: 60) |

Residues that were highly conserved among the AD domains of different AKAP proteins are indicated below by underlining with reference to the AKAP IS sequence (SEQ ID NO:15). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
                    AKAP-IS
                                              (SEQ ID NO: 15)
         QIEYLAKQIVDNAIQQA
```

Can et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIa DDD sequence of SEQ ID NO:13. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 13)
SH*IQIPP*GLT*ELLQGYT*V*EVLRQQPP*DLVE*FAVE*YFT*RLREARA*

The skilled artisan will realize that these and other amino acid substitutions in the antibody moiety or linker portions of the DNL constructs may be utilized to enhance the therapeutic and/or pharmacokinetic properties of the resulting DNL constructs.

Example 8

Cytotoxicity of RS7 Immunoconjugates to Cancer Cells

The RS7 antibody was conjugated to ranpirnase to produce an immunoconjugate with very high toxicity to a variety of epithelial cell lines. Ranpirnase (Rap) is a single-chain ribonuclease of 104 amino acids originally isolated from the oocytes of *Rana pipiens*. Rap exhibits cytostatic and cytotoxic effects on a variety of tumor cell lines in vitro, as well as antitumor activity in vivo. Rap enters cells via receptor-mediated endocytosis and once internalized into the cytosol, selectively degrades tRNA, resulting in inhibition of protein synthesis and induction of apoptosis. Rap can be administered repeatedly to patients without an untoward immune response, with reversible renal toxicity reported to be dose-limiting (Mikulski et al., J Clin Oncol 2002; 20:274-81; Int J Oncol 1993; 3:57-64).

In the studies below, an immunoconjugate comprising Rap attached to RS7 showed broad and potent anti-proliferative activity against diverse human epithelial cancer cell lines in vitro, as well as a human lung cancer xenograft in vivo. The IgG-based immunotoxin, designated 2L-Rap(Q)-hRS7, comprised Rap(Q) (a mutant form of Rap with the putative N-glycosylation site removed) conjugated to hRS7. 2L-Rap(Q)-hRS7 suppressed tumor growth in a prophylactic model of nude mice bearing Calu-3 human non-small cell lung cancer xenografts, with an increase in the median survival time (MST) from 55 to 96 days (P<0.01). The results demonstrated superior efficacy of 2L-Rap(Q)-hRS7 as a therapeutic for various Trop-2-expressing cancers, such as cervical, breast, colon, pancreatic, ovarian, and prostate cancers.

Methods

Cell Proliferation Assay

Tumor cells were seeded in 96-well plates (1×10$^4$ cells per well) and incubated with test articles at 0.01 to 100 nM for 72 h. The number of living cells was then determined using the soluble tetrazolium salt, MTS [3-(4,5-dimethylthiazol-2-yl)-5-(3-carboxymethoxyphenyl)-2-(4-sulfophenyl)-2H-tetrazolium], following the manufacturer's protocol. The data from the dose-response curves were analyzed using Graph-Pad Prism software to obtain EC50 values (the concentration at which 50% inhibition occurs).

Colony-Formation Assay

Tumor cells were trypsinized and plated in 60-mm dishes ($1 \times 10^3$ cells). Cells were treated with each test article and allowed to form colonies. Fresh media containing the test article were added every 4 days, and after 2 weeks of incubation, colonies were fixed in 4% formaldehyde and stained with Giemsa. Colonies>50 cells were enumerated under a microscope.

In Vivo Toxicity

Naïve BALB/c mice (female, 7 weeks old, Taconic Farms, Germantown, N.Y.) were injected intravenously with various doses of (Q)-hRS7 ranging from 25 to 400 μg per mouse and were monitored daily for visible signs of toxicity and body weight change. The maximum tolerated dose (MTD) was defined as the highest dose at which no deaths occurred and the body weight loss was 20% or less of pretreatment animal weight (approximately 20 g). Animals that experienced toxic effects were euthanized.

Therapeutic Efficacy in Tumor-Bearing Mice

Female NCr homozygous athymic nu/nu mice of approximately 20 g (5 weeks old when received from Taconic Farms) were inoculated s.c. with $1 \times 10^7$ Calu-3 human NSCLC cells and monitored for tumor growth by caliper measurements of length×width of the tumor. Tumor volume was calculated as (L×W2)/2. Once tumors reached approximately 0.15 cm³ in size, the animals were divided into treatment groups of five per group. Therapy consisted of either a single i.v. injection of 50 μg of (Q)-hRS7 or two injections of 25 μg administered seven days apart. A control group received saline. Animals were monitored daily for signs of toxicity and were humanely euthanized and deemed to have succumbed to disease progression if tumors reached greater than 2.0 cm³ in size or became ulcerated. Additionally, if mice lost more than 20% of initial body weight or otherwise became moribund, they were euthanized. Survival data were analyzed using Kaplan-Meier plots (log-rank analysis) with GraphPad Prism software. Differences were considered statistically significant at $P<0.05$.

Results

Binding Analysis

The reactivity of (Q)-hRS7 with Trop-2-expressing cell lines was initially assessed by ELISA and demonstrated for PC-3 and Calu-3 (data not shown), both yielding an apparent dissociation constant ($K_D$) about two-fold higher than that of hRS7 (0.28 nM vs. 0.14 nM). No binding was observed for the Trop-2-negative 22Rv1. Subsequent studies were performed by flow cytometry in a total of 10 Trop-2-expressing cell lines, and the results (not shown), indicate that there was virtually no difference in the binding property of (Q)-hRS7 from that of hRS7.

RNase Activity

The IVTT assay measures inhibition of protein synthesis due to mRNA degradation by RNase. (Q)-hRS7 and rRap exhibited comparable RNase activity in this cell-free assay (not shown). Using yeast tRNA as substrate, we estimated the kcat/Km ($10^9$ $M^{-1}$ $s^{-1}$) of rRap and (Q)-hRS7 to be 4.10 (±0.42) and 1.98, respectively. Thus the catalytic efficiency of (Q)-hRS7 based on the concentration of Rap is about 50% of rRap In Vitro Cytotoxicity Based on the results of an MTS assay, (Q)-hRS7 is most potent against ME-180, T-47D, MDA-MB-468, and Calu-3 (not shown), with EC50 values of 1.5, 2.0, 3.8, and 8.5 nM, respectively. For those cell lines showing less than <50% growth inhibition at 100 nM of (Q)-hRS7 with the MTS assay, we performed colony-formation assays to confirm that (Q)-hRS7 was cytotoxic at 10 or 100 nM to DU-145, PC-3, MCF7, SK-BR-3, BxPC-3, Capan-1, and SK-OV-3 (not shown). In both assays, hRS7, rRap, and the combination of hRS7 and rRap showed little, if any, toxicity at 100 nM in all the cell lines evaluated. The Trop-2-negative AsPC-1 was resistant to (Q)-hRS7 in both assays.

Internalization and Subcellular Location

The internalization of (Q)-hRS7 into ME-180 cells was clearly observed (not shown). The distribution pattern of intracellular (Q)-hRS7 in ME-180, as detected directly by FITC conjugated GAH or indirectly by PE-conjugated GAM via mouse anti-Rap IgG, appeared to be nearly identical, suggesting that (Q)-hRS7 remains intact following entry into these cells (not shown).

Therapeutic Efficacy in Tumor-Bearing Mice

Figure 6:
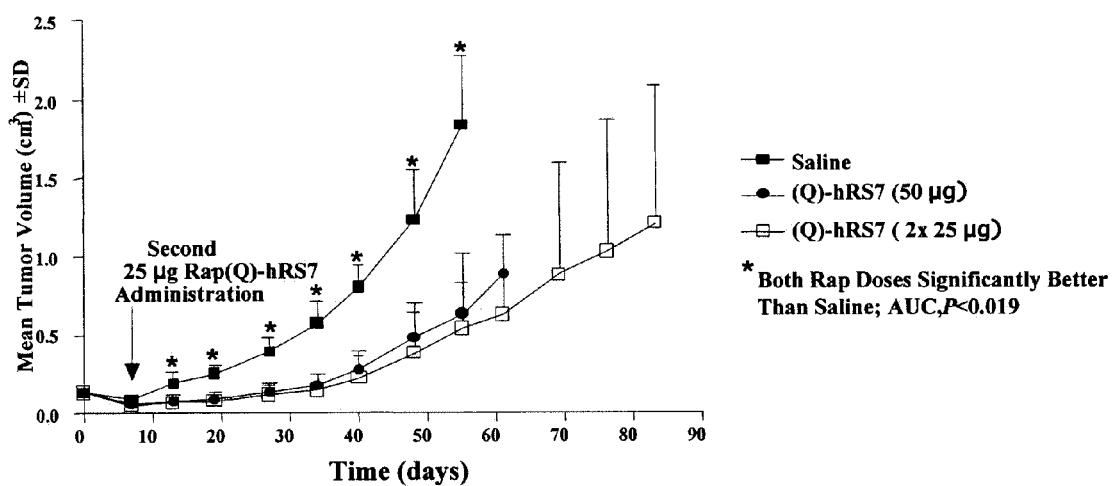
FIG. 6. Therapeutic efficacy of (Q)-hRS7 demonstrated in a Calu-3 human xenograft model to inhibit tumor growth (A) and increase MST (B). Nude mice were inoculated subcutaneously with 1×10$^7$ Calu-3 cells. When tumors reached approximately 0.15 cm$^3$, mice were treated with either a single intravenous dose of 50 µg or two injections of 25 µg administered seven days apart. Control animals received saline.
Figure 6:
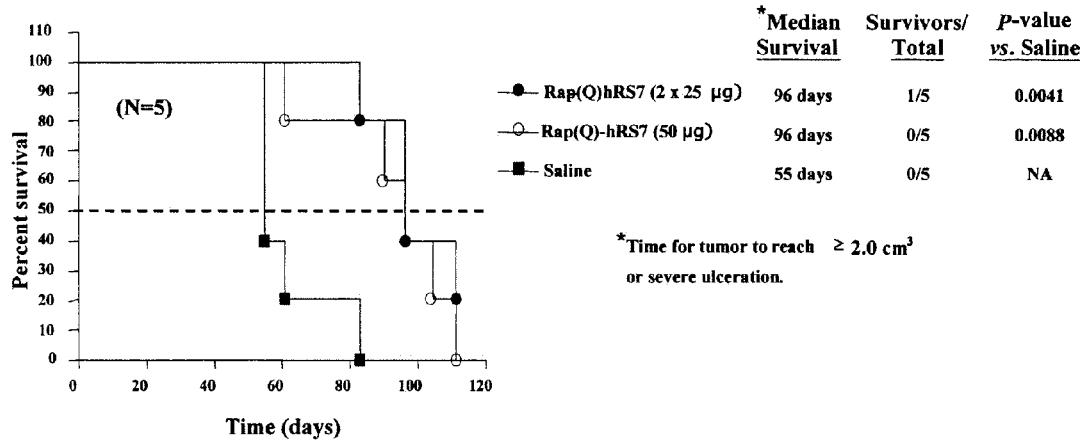

As shown in FIG. 6A, either treatment (single dose, 50 μg or two doses of 25 μg given 5 days apart) with (Q)-hRS7 significantly inhibited the growth of Calu-3 xenografts compared to untreated controls ($P<0.019$), with the median survival time increased from 55 days to 96 days ($P<0.01$; FIG. 6B).

Discussion

The clinical advancement of antibody-targeted RNases of animal origin is relatively moderate, with the majority developed for treating hematological malignancies and the targeting components conferred by some forms of scFv (Schirrmann et al., Exp Opin Biol Ther 2009; 9:79-95). To date, antibody-targeted animal RNases have not been evaluated in patients with any cancer.

Two difficulties noted in the clinical development of plant or microbial immunotoxins are undesirable toxicity and immunogenicity. Normal tissue toxicity observed with these immunotoxins includes vascular leak syndrome (VLS), hemolytic uremic syndrome (HUS), and hepatotoxicity (Kreitman, BioDrugs 2009; 23:1-13). The structural motif (x)D(y) identified to be responsible for the binding of ricin A-chain or IL-2 to endothelial cells is absent in the native sequence of Rap(Q), and hRS7 is not crossreactive with human endothelial cells. We therefore consider the likelihood of (Q)-hRS7 causing VLS to be remote. The large size of (Q)-hRS7 (~180 kDa), which poses a potential concern for less rapid penetration of tumors (Yokota et al., Cancer Res 1992; 52:3402-8), should prevent its clearance via kidneys and mitigate the risk for HUS. As for hepatotoxicity, we note that BL22, a recombinant anti-CD22 immunotoxin composed of the disulfide-stabilized Fv of RFB4 fused to PE38, and similar immunotoxins such as LMB-2 (anti-Tac(Fv)-PE38), also had a very low MTD in mice due to nonspecific liver toxicity, yet BL22 has been reported to be safe and efficacious in clinical trials of patients with hairy-cell leukemia (Kreitman et al., N Engl J Med 2001; 345:241-7). Thus, the dose-limiting hepatotoxicity commonly observed in mice may be rarely manifested in humans (Kreitman, BioDrugs 2009; 23:1-13).

Most genetically-engineered immunotoxins that have been evaluated in cancer patients induced a strong humoral immune response, which shortens the serum half-life and prevents further administration. It is expected that (Q)-hRS7 will be less immunogenic, because it comprises the fusion of a humanized antibody to a toxin (Rap) that appears to induce little antibody response in patients (Mikulski et al., J Clin Oncol 2002; 20:274-81).

Although the in vitro potency of (Q)-hRS7 was found to vary among Trop-2-expressing cell lines when measured by the 3-day MTS assay, the cytotoxicity of (Q)-hRS7 was unequivocally demonstrated at 10 nM for all cell lines using the 14-day colony-formation assay. In addition to its potent cytotoxicity against diverse cancer cell lines in vitro, (Q)-hRS7 was shown to be effective in inhibiting the growth of Calu-3 human lung cancer xenografts in nude mice, thus validating the antitumor activity and stability of (Q)-hRS7 in vivo and confirming the suitability of adding Trop-2 to the current list of antigens on solid cancers targeted by immunotoxins (Kreitman, AAPS J 2006; 8:E532-51; Pastan et al., Nat Rev Cancer 2006; Pastan et al., Ann Rev Med 2007; 58:221-37; Schirrmann et al., Exp Opin Biol Ther 2009; 9:79-95).

In conclusion, we have demonstrated that an amphibian RNase recombinantly fused with a humanized anti-Trop-2 antibody shows selective and potent cytotoxicity against a variety of epithelial cancers, both in vitro and in vivo.

Example 9

High Potency of a Rap-Anti-Trop-2 IgG DNL Construct Against Carcinomas

Using the DNL techniques described in the Examples above, an E1-Rap DNL construct, comprising hRS7-IgG-Ad2 (anti-Trop-2) linked to four copies of Rap-DDD2 was produced and showed potent in vitro growth inhibitory properties against a variety of carcinoma cell lines (not shown). In breast (MDA-MB-468), cervical (ME-180), and pancreatic (BxPC-3 and Capan-1) tumor lines, all of which express high levels of Trop-2, E1-Rap was very potent, showing $EC_{50}$ in the subnanomolar range (5 to 890 pM), which was 1,000- to 100,00-fold higher than untargeted Rap or the combination of Rap and hRS7. In cell lines expressing moderate levels of Trop-2, such as the three prostate cancer lines (PC-3, DU 145, and LNCaP), E1-Rap was less potent, but still showed $EC_{50}$ in the nanomolar range (1 to 890 nM). The cell binding data obtained for these solid cancer cell lines suggest that the sensitivity of a cell line to E1-Rap appears to correlate with its Trop-2 expression on the cell surface. No toxicity was observed for E1-Rap in the prostate cancer line, 22Rv1, which fails to bind hRS7. These results show the efficacy of E1-Rap as a new therapeutic for Trop-2-positive solid tumors, including breast, colon, stomach, lung, ovarian, endometrial, cervical, pancreatic, and prostatic carcinomas.

Example 10

Combining Antibody-Targeted Radiation (Radioimmunotherapy) and Antibody-SN-38 Conjugates (ADC) Improves Pancreatic Cancer Therapy We previously reported effective anti-tumor activity in nude mice bearing human pancreatic tumors with $^{90}$Y-humanized PAM4 IgG (hPAM4; $^{90}$Y-clivatuzumab tetraxetan) that was enhanced when combined with gemcitabine (GEM) (Gold et al., Int J. Cancer 109:618-26, 2004; Clin Cancer Res 9:3929S-37S, 2003). These studies led to clinical testing of fractionated $^{90}$Y-hPAM4 IgG combined with GEM that is showing encouraging objective responses. While GEM is known for its radiosensitizing ability, alone it is not a very effective therapeutic agent for pancreatic cancer and its dose is limited by hematologic toxicity, which is also limiting for $^{90}$Y-hPAM4 IgG.

We have observed promising anti-tumor activity with an ADC composed of hRS7 IgG (humanized anti-epithelial glycoprotein-1; EGP-1) and SN-38, the active component of irinotecan. This ADC is very well tolerated in mice (e.g., ≥60 mg), yet just 4.0 mg (0.5 mg, twice-weekly×4) is significantly therapeutic. EGP-1 (Trop2) is also expressed in most pancreatic cancers.

The present study examined combinations of $^{90}$Y-hPAM4 IgG with RS7-SN-38 in nude mice bearing 0.35 cm$^3$ subcutaneous xenografts of the human pancreatic cancer cell line, Capan-1. Mice (n=10) were treated with a single dose of $^{90}$Y-hPAM4 IgG alone (130 µCi, i.e., the maximum tolerated dose (MTD) or 75 Ci), with RS7-SN-38 alone (as above), or combinations of the 2 agents at the two $^{90}$Y-hPAM4 dose levels, with the first ADC injection given the same day as the $^{90}$Y-hPAM4. All treatments were tolerated, with ≤15% loss in body weight. Objective responses occurred in most animals, but they were more robust in both of the combination groups as compared to each agent given alone. All animals in the 0.13-mCi $^{90}$Y-hPAM4 IgG+hRS7-SN-38 group achieved a tumor-free state within 4 weeks, while other animals continued to have evidence of persistent disease. These studies provide the first evidence that combined radioimmunotherapy and ADC enhances efficacy at safe doses.

In the ongoing PAM4 clinical trials, a four week clinical treatment cycle is performed. In week 1, subjects are administered a dose of $^{111}$In-hPAM4, followed at least 2 days later by gemcitabine dose. In weeks 2, 3 and 4, subjects are administered a $^{90}$Y-hPAM4 dose, followed at least 2 days later by gemcitabine (200 mg/m$^2$). Escalation started at 3×6.5 mCi/m$^2$. The maximum tolerated dose in front-line pancreatic cancer patients was 3×15 mCi/m$^2$ (hematologic toxicity is dose-limiting). Of 22 CT-assessable patients, the disease control rate (CR+PR+SD) was 68%, with 5 (23%) partial responses and 10 (45%) having stabilization as best response by RECIST criteria.

Preparation of Antibody-Drug Conjugate (ADC)

Figure 7:
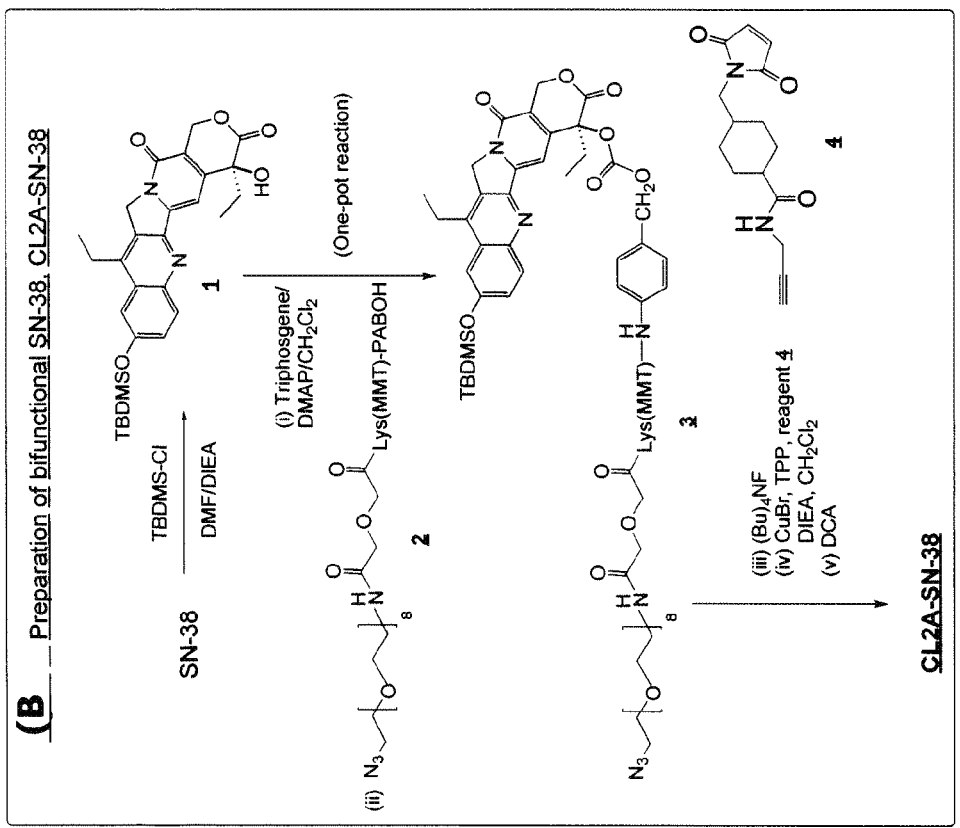
FIG. 7 illustrates (A) the structure of bifunctional SN-38 (CL2A-SN-38); (B) a synthetic scheme for preparing CL2A-SN-38; and (C) a conjugation scheme for attaching CL2A-SN-38 to an antibody.
Figure 7:
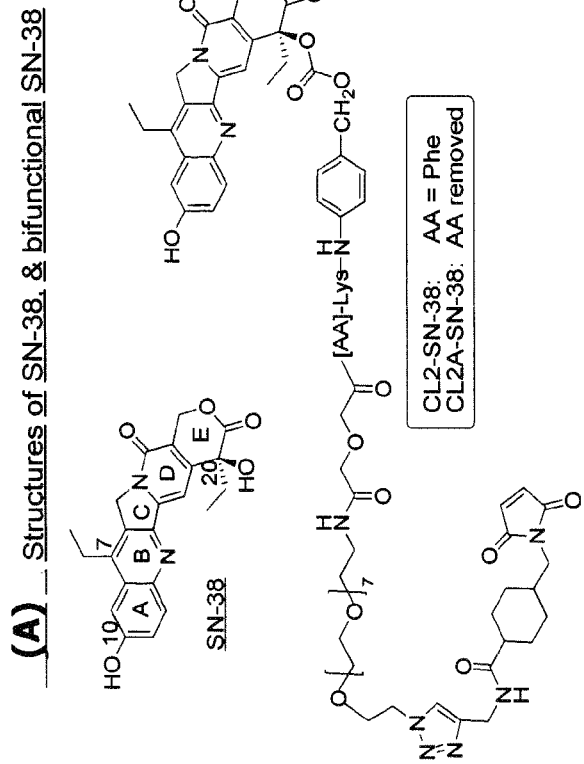
Figure 7:
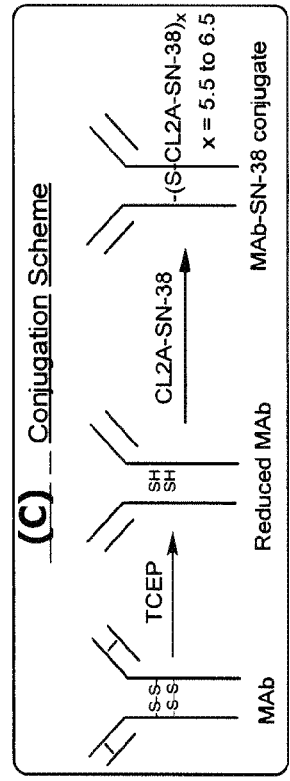

The SN-38 conjugated hRS7 antibody was prepared as shown in FIG. 7 and according to previously described protocols (Moon et al. J Med Chem 2008, 51:6916-6926; Govindan et al., Clin Cancer Res 2009. 15:6052-6061). A reactive bifunctional derivative of SN-38 (CL2A-SN-38, FIG. 7A) was prepared as described in U.S. Patent Application Publ. No. 20200204589 (the Examples section of which is incorporated herein by reference). The formula of CL2A-SN-38 is (maleimido-[x]-Lys-PABOCO-20-O—SN-38, where PAB is p-aminobenzyl and 'x' contains a short PEG). The synthetic scheme for CL2A-SN-38 production is further illustrated in FIG. 7B. Following reduction of disulfide bonds in the antibody with TCEP, the CL2A-SN-38 is reacted with reduced antibody to generate the SN-38 conjugated RS7 (FIG. 7C).

$^{90}$Y-hPAM4 is prepared as previously described (Gold et al., Clin Cancer Res 2003, 9:3929S-37S; Gold et al., Int J Cancer 2004, 109:618-26).

Combination RAIT+ADC

The hRS7 is present in most epithelial cancers (lung, breast, prostate, ovarian, colorectal, pancreatic) and hRS7-SN-38 conjugates are being examined in various human cancer-mouse xenograft models. Initial clinical trials with $^{90}$Y-hPAM4 IgG plus radiosensitizing amounts of GEM are encouraging, with evidence of tumor shrinkage or stable disease. However, therapy of pancreatic cancer is very challenging. Therefore, a combination therapy was examined to determine whether it would response. Specifically, administration of hRS7-SN-38 at effective, yet non-toxic doses was combined with RAIT with $^{90}$Y-hPAM4 IgG.

Figure 8:
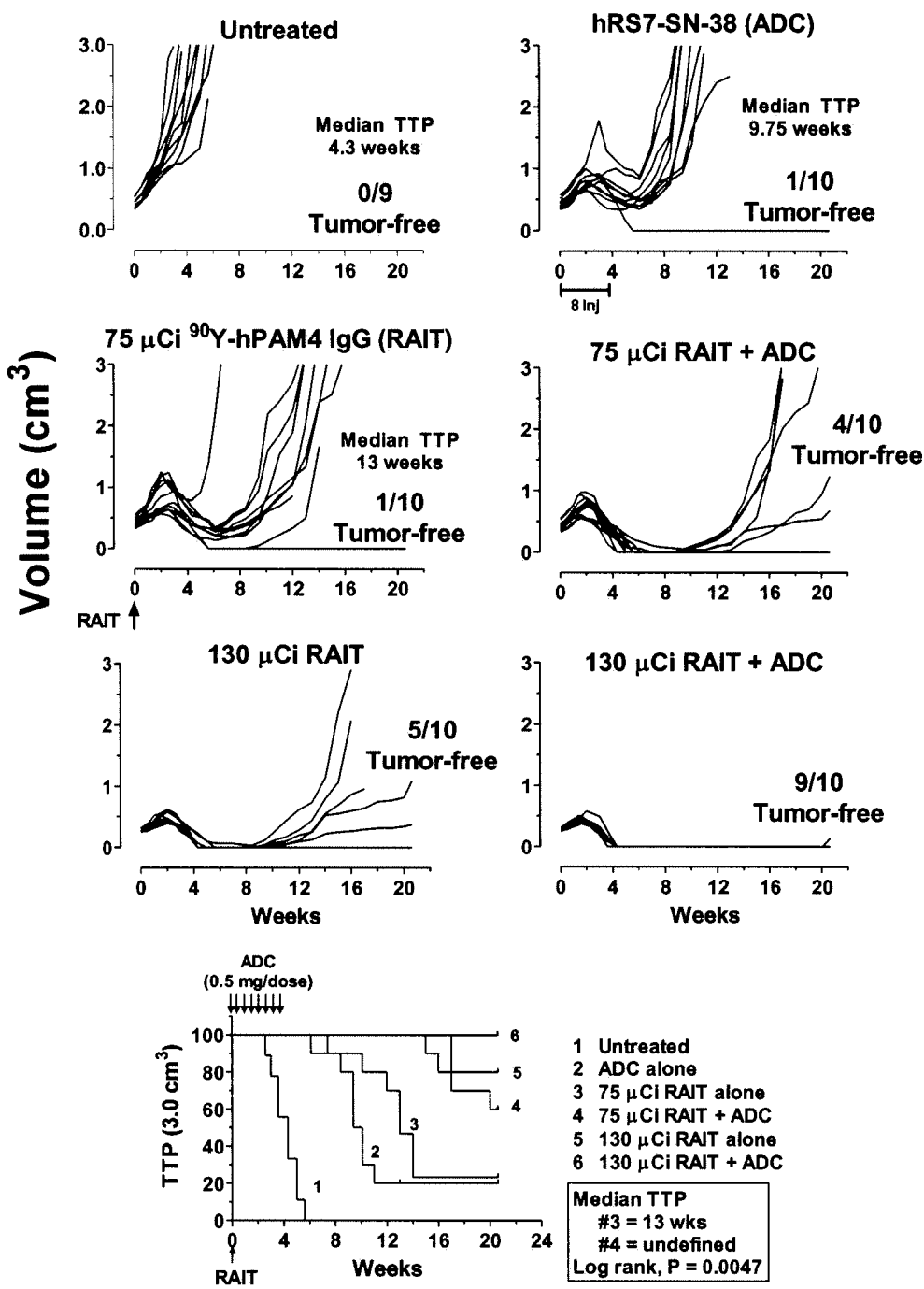
FIG. 8 compares the therapeutic efficacy of hRS7-SN-38 alone, $^{90}$Y-hPAM4 alone, and the combination of hRS7-SN-38 and $^{90}$Y-hPAM4, at either 75 µCi or 130 µCi.

The results shown in FIG. 8 demonstrate that the combination of hRS7-SN-38 with $^{90}$Y-hPAM4 was more effective than either treatment alone, or the sum of the individual treatments. At a dosage of 75 µCi $^{90}$Y-hPAM4, only 1 of 10 mice was tumor-free after 20 weeks of therapy, the same as observed with hRS7-SN-38 alone. However, the combination of hRS7-SN-38 with $^{90}$Y-hPAM4 resulted in 4 of 10 mice that were tumor-free after 20 weeks, and the remaining subjects showed substantial decrease in tumor volume compared with either treatment alone. At 130 µCi $^{90}$Y-hPAM4 the difference was even more striking, with 9 of 10 animals tumor-free in the combined therapy group compared to 5 of 10 in the RAIT alone group. These data demonstrate the synergistic effect of the combination of hRS7-SN-38 with $^{90}$Y-hPAM4. RAIT+ADC significantly improved time to progression and increased the frequency of tumor-free treatment.

Figure 9:
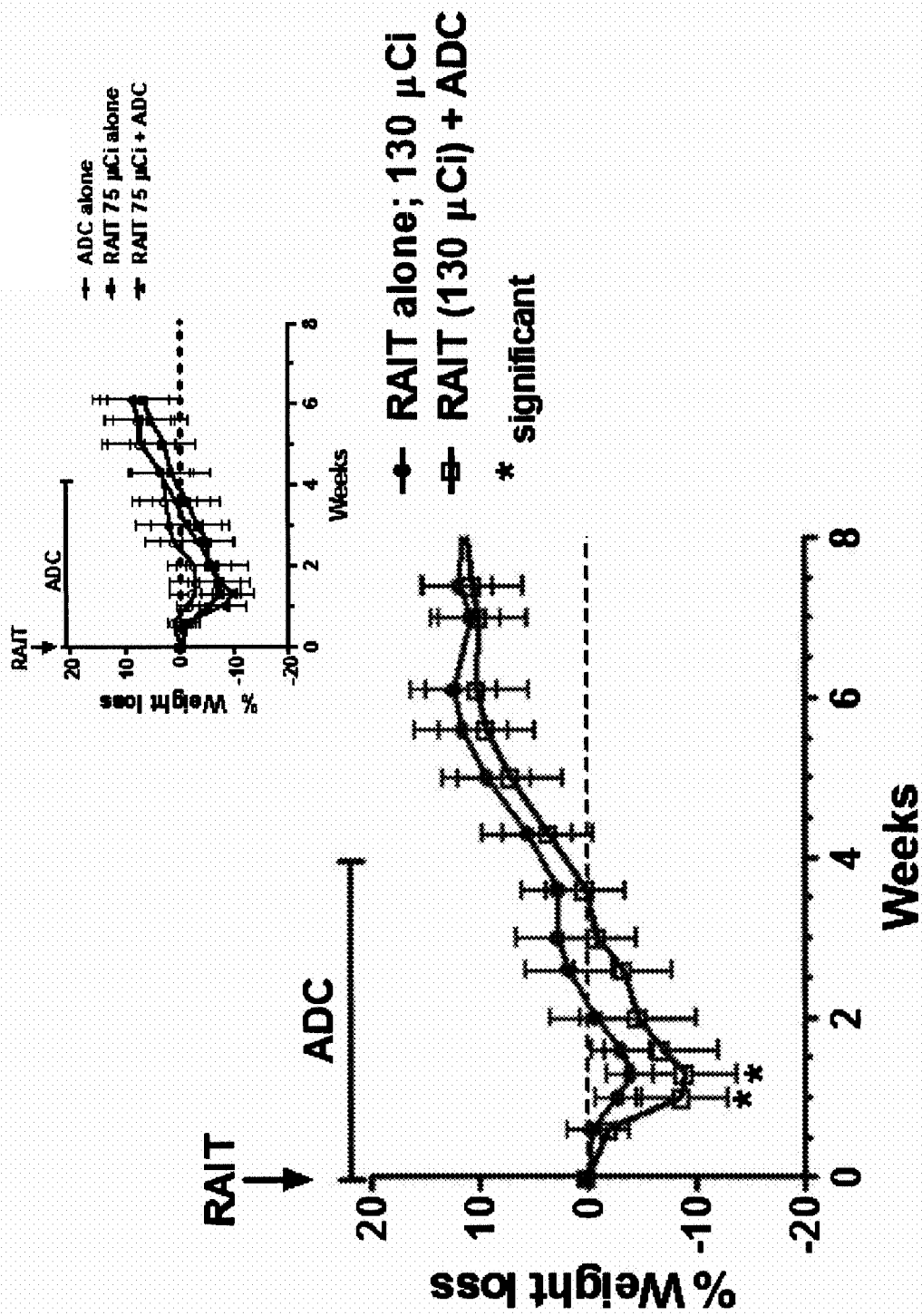
FIG. 9 illustrates the toxicity, measured as % weight loss, of RAIT alone and ADC alone versus the combination of RAIT plus ADC.

FIG. 9 shows that the combination of ADC with hRS7-SN-38 added to the MTD of RAIT with $^{90}$Y-hPAM4 had minimal additional toxicity, indicated by the % weight loss of the animal in response to treatment.

Figure 10:
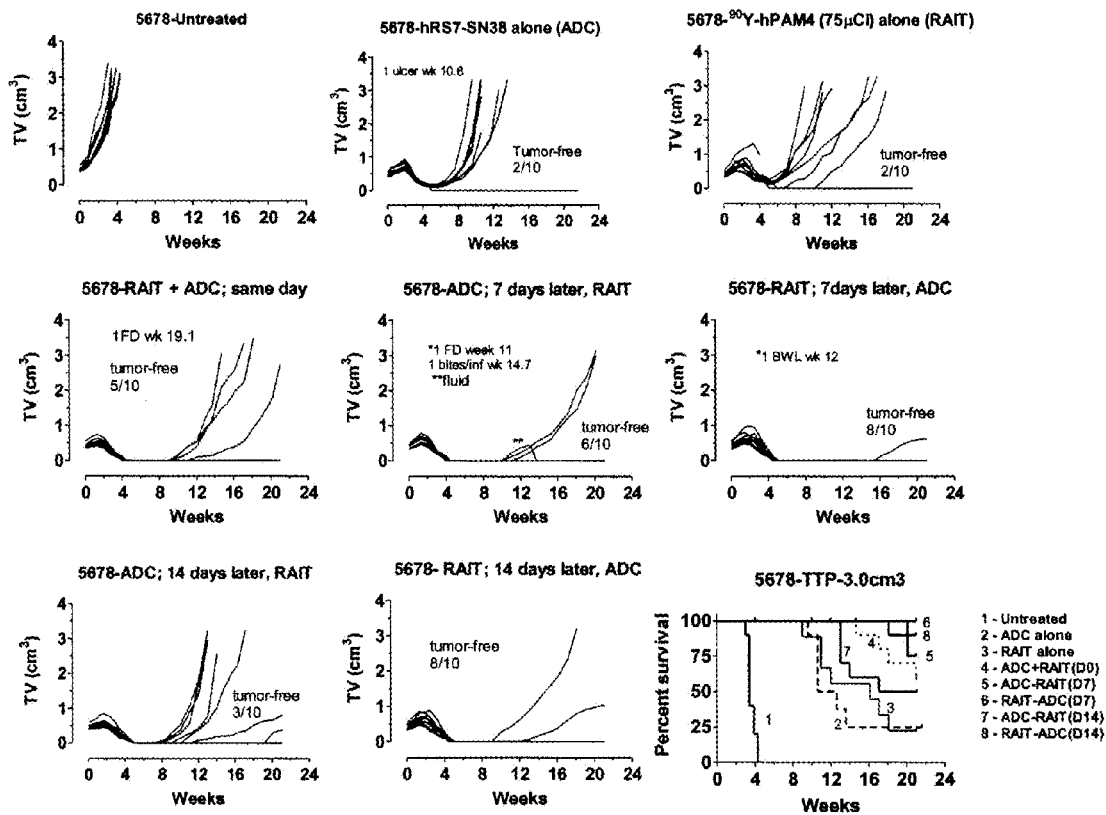
FIG. 10 compares the effects of simultaneous RAIT and ADC with sequential administration of the two treatments.
Figure 10:
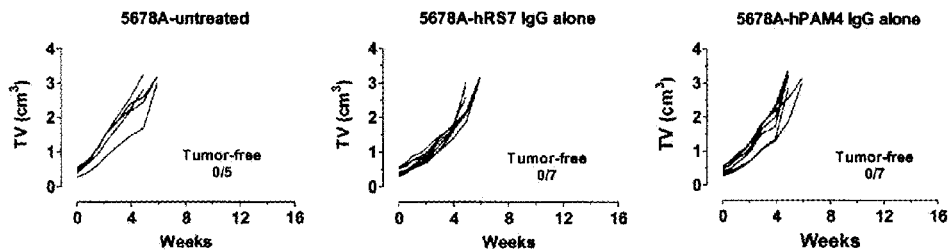

The effect of different sequential treatments on tumor survival is illustrated in FIG. 10. The results indicate that the optimal effect is obtained when RAIT is administered first, followed by ADC. In contrast, when ADC is administered first followed by RAIT, there is a decrease in the incidence of tumor-free animals. Neither unconjugated hPAM4 nor hRS7 antibodies had anti-tumor activity when given alone.

Figure 11:
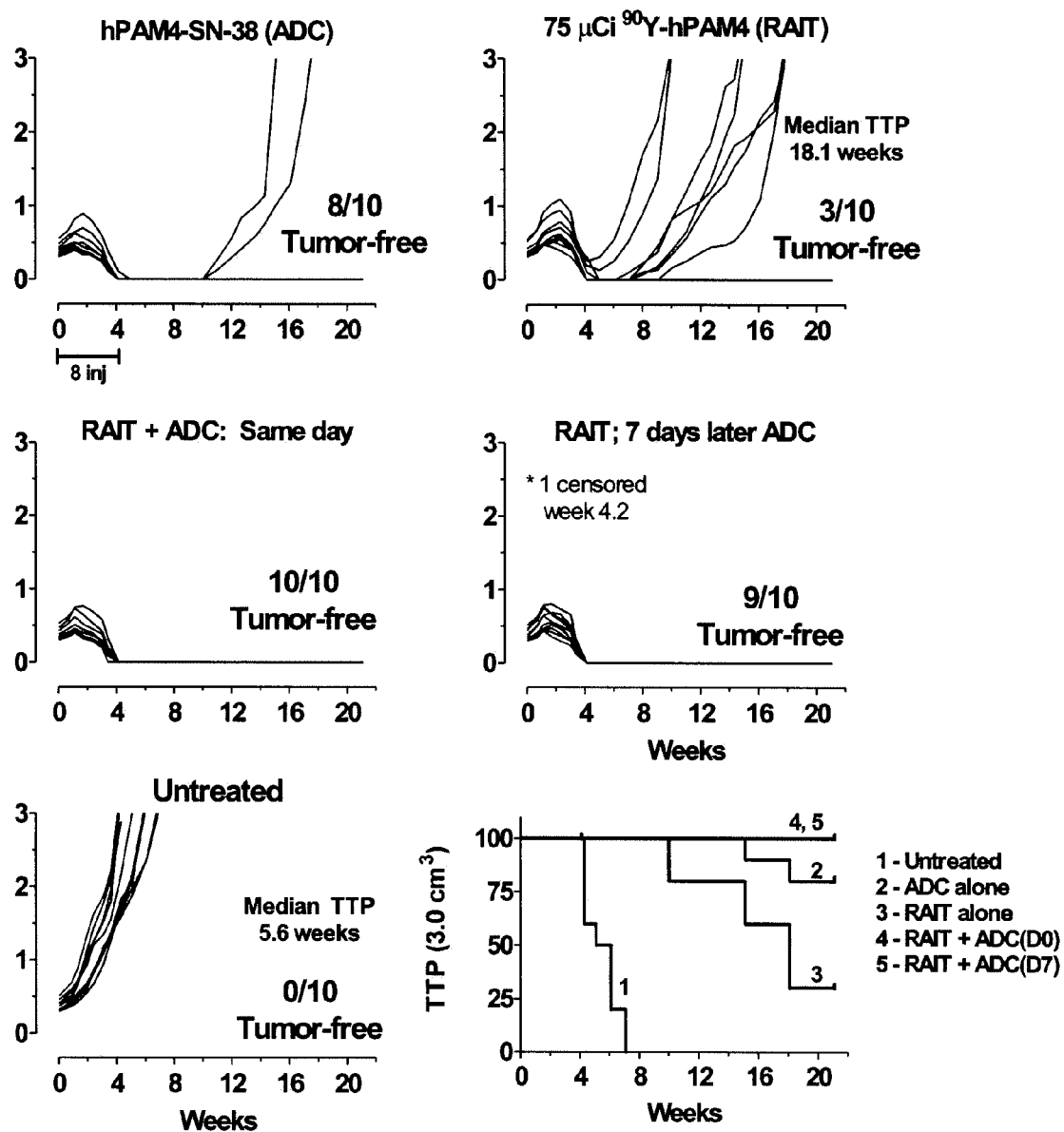
FIG. 11 shows the effects of RAIT and ADC performed with the same (hPAM4) antibody.

Experiments were performed in which both the radionuclide and the drug (SN-38) were conjugated to the same (PAM4) antibody. FIG. 11 shows that a 0.5 mg dose of hPAM4-SN-38, given twice weekly for 8 weeks, was relatively effective at inhibiting tumor growth. However, addition of $^{90}$Y-hPAM4 either on the same day or else prior to ADC improved the incidence of tumor-free animals at 12 weeks. These results show that RAIT and ADC treatments targeting the same antigen can be given together. Even though hPAM4 IgG does not internalize, hPAM4-SN-38 conjugate controlled tumor growth longer than hRS7-SN-38 in this model system (which expresses high levels of PAM4 antigen).

Example 11

Efficacy of SN-38 Conjugates of Different Antibodies

CL2A-SN-38 was conjugated to humanized antibodies, hRS7 (anti-EGP-1), hPAM4 (anti-mucin), hMN-14 (anti-CEACAM5), hLL2 (anti-CD22), and hA20 (anti-CD20). The conjugates, with a mean SN-38/MAb substitution (MSR) of ~6, were evaluated in the Capan-1 and BxPC-3 pancreatic human tumor xenografts and the Ramos human lymphoma xenograft grown s.c. in female athymic nude mice. When the starting tumor sizes in animals reached 0.2 to 0.3 cm$^3$, specific and non-targeting control conjugates were administered i.p. in a twice-weekly×4 weeks schedule using 25 mg/kg, 12.5 mg/kg, or 5 mg/kg of protein dose.

All of the SN-38 antibody conjugates showed efficacy when examined in an appropriate target cancer cell line (data not shown). The hMN-14-SN-38 conjugate showed efficacy against LS174T human colon carcinoma xenograft in nude mice (not shown). The hA20-SN-38 and hLL2 conjugates showed efficacy in against Ramos human lymphoma xenografts in nude mice (not shown). The hRS7-SN-38 and hPAM4-SN-38 conjugates showed efficacy against Capan-1 human pancreatic cancer xenografts in nude mice (not shown).

Figure 12:
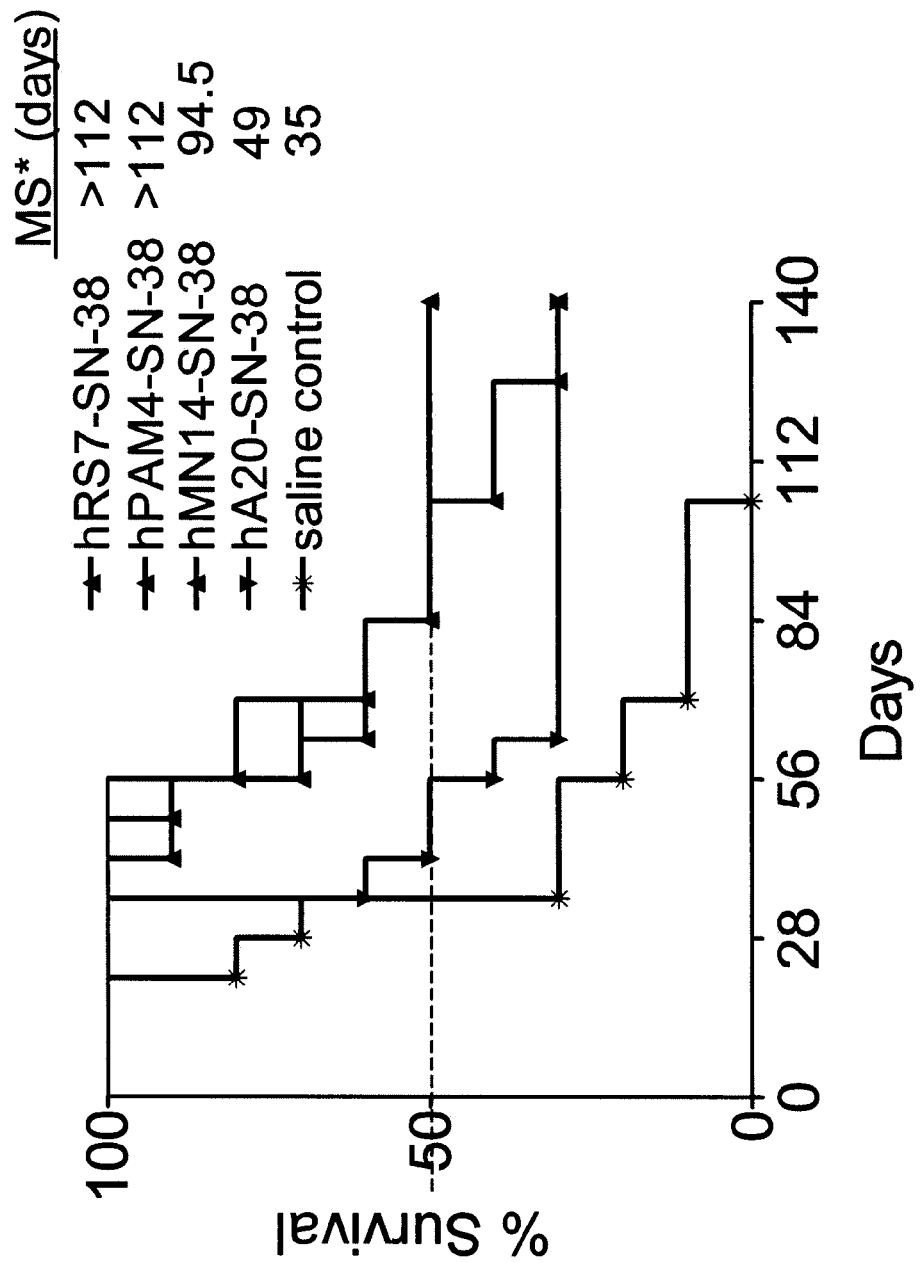
FIG. 12 indicates the comparative efficacies of different antibody conjugates of SN-38.

A comparison was performed of the efficacy of SN-38 conjugates of hRS7, hPAM4, hMN14 and the control hA20 antibodies against Capan-1 human pancreatic cancer xenografts in nude mice. As shown in FIG. 12, the hRS7 and hPAM4 conjugates of SN-38 showed the greatest efficacy against a human pancreatic cancer cell line.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

---

What is claimed is:

1. A method of treating a cancer that expresses Trop-2 and MUC-5ac comprising
    a) administering to a subject with a cancer that expresses Trop-2 and MUC-5ac an anti-Trop-2 antibody or antigen-binding fragment thereof conjugated to SN-38; and
    b) administering to said subject an anti-MUC-5ac antibody or antigen-binding fragment thereof conjugated to $^{90}Y$;
wherein the combination of drug-conjugated anti-Trop-2 and radionuclide-conjugated anti-MUC-5 ac antibodies is effective to treat the cancer.

2. The method of claim 1, wherein the anti-Trop-2 antibody or antigen-binding fragment thereof binds to the same epitope as an anti-Trop-2 antibody comprising the light chain CDR sequences CDR1 (KASQDVSIAVA, SEQ ID NO:7); CDR2 (SASYRYT, SEQ ID NO:8); and CDR3 (QQHYITPLT, SEQ ID NO:9) and the heavy chain CDR sequences CDR1 (NYGMN, SEQ ID NO:10); CDR2 (WINTYTGEPTYTDDFKG, SEQ ID NO:11) and CDR3 (GGFGSSYWYFDV, SEQ ID NO:12).

3. The method of claim 1, wherein the anti-MUC-5ac antibody or fragment thereof binds to the same epitope as an anti-MUC-5ac antibody comprising the light complementarity determining region (CDR) sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6).

4. The method of claim 1, wherein the anti-Trop-2 antibody or antigen-binding fragment thereof comprises the light chain CDR sequences CDR1 (KASQDVSIAVA, SEQ ID NO:7); CDR2 (SASYRYT, SEQ ID NO:8); and CDR3 (QQHYITPLT, SEQ ID NO:9) and the heavy chain CDR sequences CDR1 (NYGMN, SEQ ID NO:10); CDR2 (WINTYTGEPTYTDDFKG, SEQ ID NO:11) and CDR3 (GGFGSSYWYFDV, SEQ ID NO:12).

5. The method of claim 1, wherein the anti-MUC-5ac antibody or fragment thereof comprises the light complementarity determining region (CDR) sequences CDR1 (SASSSVSSSYLY, SEQ ID NO:1); CDR2 (STSNLAS, SEQ ID NO:2); and CDR3 (HQWNRYPYT, SEQ ID NO:3); and the heavy chain CDR sequences CDR1 (SYVLH, SEQ ID NO:4); CDR2 (YINPYNDGTQYNEKFKG, SEQ ID NO:5) and CDR3 (GFGGSYGFAY, SEQ ID NO:6).

6. The method of claim 1, wherein the anti-Trop-2 antibody or fragment thereof and the anti-MUC-5ac antibody or fragment thereof are administered sequentially or concurrently.

7. The method of claim 1, wherein the anti-Trop-2 antibody or fragment thereof and the anti-MUC-5ac antibody or fragment thereof are conjugated together.

8. The method of claim 1, wherein the anti-Trop-2 antibody or fragment thereof and the anti-MUC-5ac antibody or fragment thereof are chimeric, humanized or human antibodies or fragments thereof.

9. The method of claim 1, further comprising administering to the subject a therapeutic agent selected from the group consisting of a chemotherapeutic drug, an immunomodulator, a hormone, a hormone antagonist, an enzyme, an siRNA, an RNAi, a photoactive therapeutic agent, an anti-angiogenic agent, a pro-apoptotic agent, an antibody and an antigen-binding antibody fragment.

10. The method of claim 9, wherein the immunomodulator is selected from the group consisting of a cytokine, a lymphokine, a monokine, a stem cell growth factor, a lymphotoxin, a hematopoietic factor, a colony stimulating factor (CSF), an interferon (IFN), parathyroid hormone, thyroxin, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (ILGF), erythropoietin, thrombopoietin, TNF-α, TNF-β, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin and endostatin.

11. The method of claim 9, wherein the chemotherapeutic drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, *vinca* alkaloids, substituted ureas, methyl hydrazine derivatives, adrenocortical suppressants, hormone antagonists, endostatin, taxols, camptothecins, SN-38, doxorubicin, doxorubicin analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate and CPT-11.

12. The method of claim 9, wherein the antibody or antigen-binding antibody fragment binds to an antigen selected from the group consisting of CA19.9, DUPAN2, SPAN1, Nd2, B72.3, CC49, $Le^a$, Le(y), CEACAM5, CEACAM6, CSAp, MUC-1, MUC-2, MUC-3, MUC-4, MUC-5ac, MUC-16, MUC-17, HLA-DR, CD40, CD74, CD138, HER2/neu, EGFR, EGP-1, EGP-2, VEGF, P1GF, insulin-like growth factor, tenascin, platelet-derived growth factor, IL-6, bcl-2, K-ras, p53 and cMET.

* * * * *

SEQUENCE LISTING

```
<160> NUMBER OF SEQ ID NOS: 60

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ala Ser Ser Ser Val Ser Ser Ser Tyr Leu Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Thr Ser Asn Leu Ala Ser
1               5

<210> SEQ ID NO 3
<211> LENGTH: 9
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 3

His Gln Trp Asn Arg Tyr Pro Tyr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Val Leu His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Asn Pro Tyr Asn Asp Gly Thr Gln Tyr Asn Glu Lys Phe Lys
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Gly Gly Ser Tyr Gly Phe Ala Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Ser Gln Asp Val Ser Ile Ala Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ser Ala Ser Tyr Arg Tyr Thr
1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Gln Gln His Tyr Ile Thr Pro Leu Thr
1               5
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Asn Tyr Gly Met Asn
1               5
```

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Trp Ile Asn Thr Tyr Thr Gly Glu Pro Thr Tyr Thr Asp Asp Phe Lys
1               5                   10                  15

Gly
```

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Gly Gly Phe Gly Ser Ser Tyr Trp Tyr Phe Asp Val
1               5                   10
```

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
```

```
                35                  40

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ile Glu Tyr Leu Ala Lys Gln Ile Val Asp Asn Ala Ile Gln Gln
1               5                   10                  15

Ala

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 17
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50
```

```
<210> SEQ ID NO 18
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 20
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25
```

<210> SEQ ID NO 22
<211> LENGTH: 51
<212> TYPE: PRT
<213> ORGANISM: Homo sapiens

<400> SEQUENCE: 22

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 23
<211> LENGTH: 54
<212> TYPE: PRT
<213> ORGANISM: Homo sapiens

<400> SEQUENCE: 23

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 24
<211> LENGTH: 44
<212> TYPE: PRT
<213> ORGANISM: Homo sapiens

<400> SEQUENCE: 24

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 25
<211> LENGTH: 44
<212> TYPE: PRT
<213> ORGANISM: Homo sapiens

<400> SEQUENCE: 25

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 26
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 26

Gln Ile Glu Tyr Val Ala Lys Gln Ile Val Asp Tyr Ala Ile His Gln
1               5                   10                  15

Ala

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ile Glu Tyr Lys Ala Lys Gln Ile Val Asp His Ala Ile His Gln
1               5                   10                  15

Ala

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ile Glu Tyr His Ala Lys Gln Ile Val Asp His Ala Ile His Gln
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ile Glu Tyr Val Ala Lys Gln Ile Val Asp His Ala Ile His Gln
1               5                   10                  15

Ala

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Leu Glu Tyr Gln Ala Gly Leu Leu Val Gln Asn Ala Ile Gln Gln
1               5                   10                  15

Ala Ile

<210> SEQ ID NO 31
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 31

Leu Leu Ile Glu Thr Ala Ser Ser Leu Val Lys Asn Ala Ile Gln Leu
1               5                   10                  15

Ser Ile

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Ile Glu Glu Ala Ala Ser Arg Ile Val Asp Ala Val Ile Glu Gln
1               5                   10                  15

Val Lys

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Leu Tyr Gln Phe Ala Asp Arg Phe Ser Glu Leu Val Ile Ser Glu
1               5                   10                  15

Ala Leu

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Glu Gln Val Ala Asn Gln Leu Ala Asp Gln Ile Ile Lys Glu Ala
1               5                   10                  15

Thr

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Glu Glu Leu Ala Trp Lys Ile Ala Lys Met Ile Trp Ser Asp Val
1               5                   10                  15

Phe

<210> SEQ ID NO 36
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Leu Val Arg Leu Ser Lys Arg Leu Val Glu Asn Ala Val Leu Lys
1               5                   10                  15

Ala Val

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Glu Glu Val Ser Ala Arg Ile Val Gln Val Val Thr Ala Glu
1               5                   10                  15

Ala Val

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Lys Gln Ala Ala Phe Gln Leu Ile Ser Gln Val Ile Leu Glu
1               5                   10                  15

Ala Thr

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ala Trp Lys Ile Ala Lys Met Ile Val Ser Asp Val Met Gln Gln
1               5                   10                  15

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 41
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Gln Tyr Ala Asn Gln Leu Ala Asp Gln Ile Ile Lys Glu Ala
1               5                   10                  15

Thr Glu

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Glu Glu Leu Ala Trp Lys Ile Ala Lys Met Ile Trp Ser Asp Val
1               5                   10                  15

Phe Gln Gln Cys
            20

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Pro Asp Asn Ala Ile Gln Gln
1               5                   10                  15

Ala

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25
```

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 52
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 53
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 55
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 55

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Gln Asp Lys Asn Tyr Glu Asp Glu Leu Thr Gln Val Ala Leu Ala
1               5                   10                  15

Leu Val Glu Asp Val Ile Asn Tyr Ala
```

```
<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Thr Ser Ala Lys Asp Asn Ile Asn Ile Glu Glu Ala Ala Arg Phe
1               5                   10                  15

Leu Val Glu Lys Ile Leu Val Asn His
            20                  25
```